(12) United States Patent  
Maryanka

(10) Patent No.: US 9,205,239 B2
(45) Date of Patent: Dec. 8, 2015

(54) NASAL CAVITY DILATOR DEVICE

(71) Applicant: ASAP BreatheAssist Pty Ltd, Armadale (AU)

(72) Inventor: Paz Maryanka, South Yarra (AU)

(73) Assignee: ASAP Breathe Assist Pty Ltd., Victoria (AU)

( * ) Notice: Subject to any disclaimer, the term of this patent is extended or adjusted under 35 U.S.C. 154(b) by 0 days.

(21) Appl. No.: 14/506,425

(22) Filed: Oct. 3, 2014

(65) Prior Publication Data

US 2015/0080936 A1     Mar. 19, 2015

Related U.S. Application Data

(63) Continuation of application No. 12/154,868, filed on May 28, 2008, now abandoned, which is a continuation-in-part of application No. 11/363,884, filed on Feb. 28, 2006, now Pat. No. 7,740,643, which is a continuation of application No. 10/631,415, filed on Jul. 30, 2003, now Pat. No. 7,105,008, which is a continuation-in-part of application No. PCT/AU03/00504, filed on Apr. 30, 2003.

(51) Int. Cl.
*A61F 2/18* (2006.01)
*A61M 29/00* (2006.01)
*A61F 5/08* (2006.01)
*A61M 15/08* (2006.01)
*A61B 17/24* (2006.01)
*A61F 5/56* (2006.01)

(52) U.S. Cl.
CPC ............... *A61M 29/00* (2013.01); *A61B 17/24* (2013.01); *A61F 5/08* (2013.01); *A61F 5/56* (2013.01); *A61M 15/085* (2014.02); *A61B 2017/248* (2013.01)

(58) Field of Classification Search
CPC ... A61F 2/186; A61F 13/2005; A61F 13/126; A61F 5/08; A61M 2210/0681; A61M 2210/0618; A61M 15/85; A61M 15/08; A61M 16/0666
USPC .................. 606/196, 199, 204.45; 623/10
See application file for complete search history.

(56) References Cited

U.S. PATENT DOCUMENTS 1,034,566 A * 8/1912 Barratt .......................... 606/199
3,710,799 A    1/1973 Caballero
(Continued)

FOREIGN PATENT DOCUMENTS

JP            11192251        7/1999
WO        WO 00/78223      12/2000
WO      WO 2004/026391      4/2004

OTHER PUBLICATIONS

Oct. 23, 2014 Office Action, issued in connection with U.S. Appl. No. 12/154,868.

(Continued)

*Primary Examiner* — Christopher D Prone
(74) *Attorney, Agent, or Firm* — Gary J. Gershik; Cooper & Dunham LLP

(57) ABSTRACT

An improved adjustable nasal dilator device insertable within the nasal cavity of a human being to improve the flow of air through the nasal passage. The device includes a body, a top and bottom frame ends interconnected by a series of spaced flexible ribs. The top and bottom frame ends are open and substantially circular, and the diameter of the bottom frame end is greater than the corresponding diameter of the top frame end to provide a body shape for convenient insertion within a nasal cavity.

15 Claims, 40 Drawing Sheets

(56) References Cited

U.S. PATENT DOCUMENTS

| | | | |
|---|---|---|---|
| 4,576,168 | A | 3/1986 | Jalowayski |
| 4,759,365 | A | 7/1988 | Askinazy |
| 5,059,193 | A | 10/1991 | Kuslich |
| 5,423,858 | A | 6/1995 | Bolanos et al. |
| 5,683,465 | A | 11/1997 | Shinn et al. |
| 5,693,100 | A | 12/1997 | Pisharodi |
| 5,895,409 | A | 4/1999 | Mehdizadeh |
| 6,129,763 | A | 10/2000 | Chauvin et al. |
| 6,270,512 | B1 | 8/2001 | Rittmann |
| 6,436,142 | B1 | 8/2002 | Paes et al. |
| 6,821,298 | B1 | 11/2004 | Jackson |
| 7,105,008 | B2 | 9/2006 | Maryanka |
| 7,727,252 | B2 | 6/2010 | Maryanka |
| 7,740,643 | B2 | 6/2010 | Maryanka |
| 2005/0278028 | A1 | 12/2005 | Mujwid |

OTHER PUBLICATIONS

International Preliminary Examination Report, completed Feb. 2, 2005 in connection with PCT International Patent Application No. PCT/AU2003/000504.

Mar. 14, 2005 Office Action, issued in connection with U.S. Appl. No. 10/631,415.

Jun. 14, 2005 Response, filed in connection with U.S. Appl. No. 10/631,415.

Aug. 18, 2005 Office Action, issued in connection with U.S. Appl. No. 10/631,415.

Oct. 25, 2005 Response, filed in connection with U.S. Appl. No. 10/631,415.

Dec. 29, 2005 Office Action, issued in connection with U.S. Appl. No. 10/631,415.

Jan. 4, 2006 Response, filed in connection with U.S. Appl. No. 10/631,415.

Oct. 27, 2008 Office Action, issued in connection with U.S. Appl. No. 11/363,924.

Feb. 11, 2009 Response, filed in connection with U.S. Appl. No. 11/363,924.

Apr. 13, 2009 Office Action, issued in connection with U.S. Appl. No. 11/363,924.

Sep. 4, 2009 Response, filed in connection with U.S. Appl. No. 11/363,924.

Oct. 27, 2008 Office Action, issued in connection with U.S. Appl. No. 11/363,884.

Feb. 11, 2009 Response, filed in connection with U.S. Appl. No. 11/363,884.

May 14, 2009 Office Action, issued in connection with U.S. Appl. No. 11/363,884.

Nov. 5, 2009 Response, filed in connection with U.S. Appl. No. 11/363,884.

Porex Corporation Website, Surgical Nostril Retainers, Dec. 19, 2005, http/www.porexurgical.com/English/surgical/sprodnoseother.asp.

Feb. 20, 2009 Notice of Abandonment, issued in connection with U.S. Appl. No. 12/154,868.

Mar. 10, 2014 Petition to Revive an Unintentionally Abandoned Application, filed in connection with U.S. Appl. No. 12/154,868.

Jun. 12, 2014 Office Action, issued in connection with U.S. Appl. No. 12/154,868.

* cited by examiner

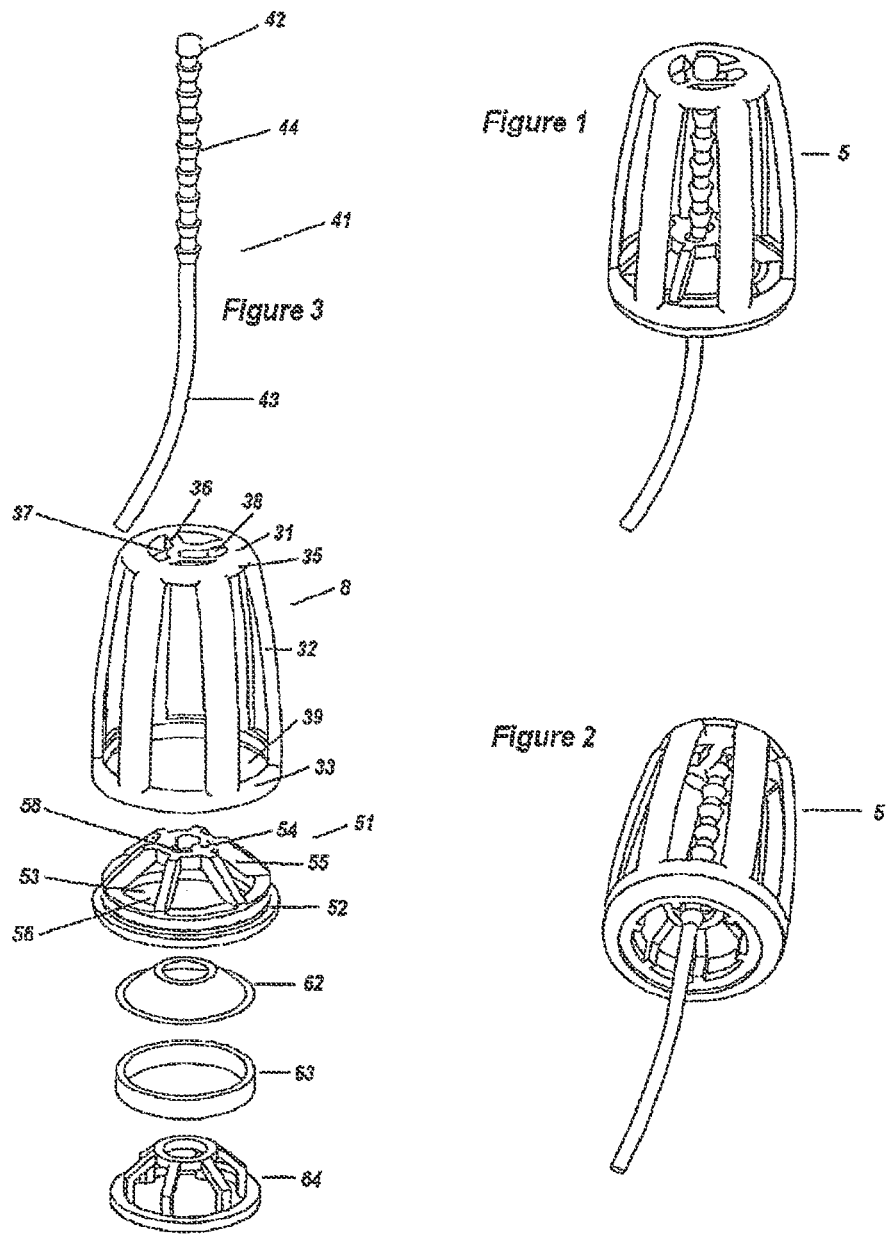

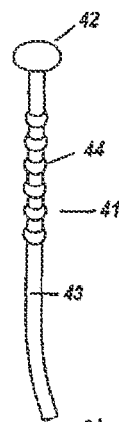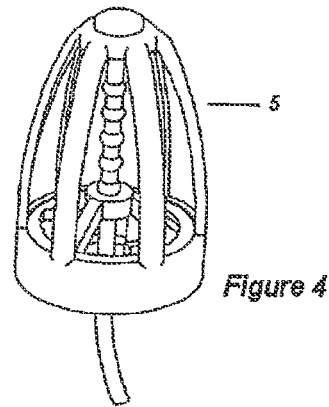
Figure 4
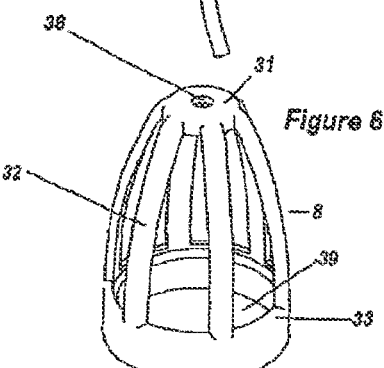
Figure 6
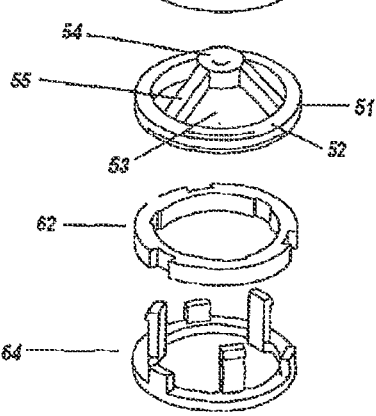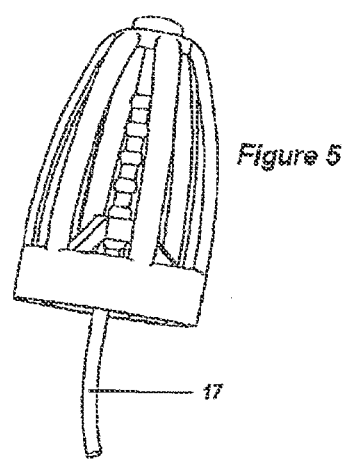
Figure 5

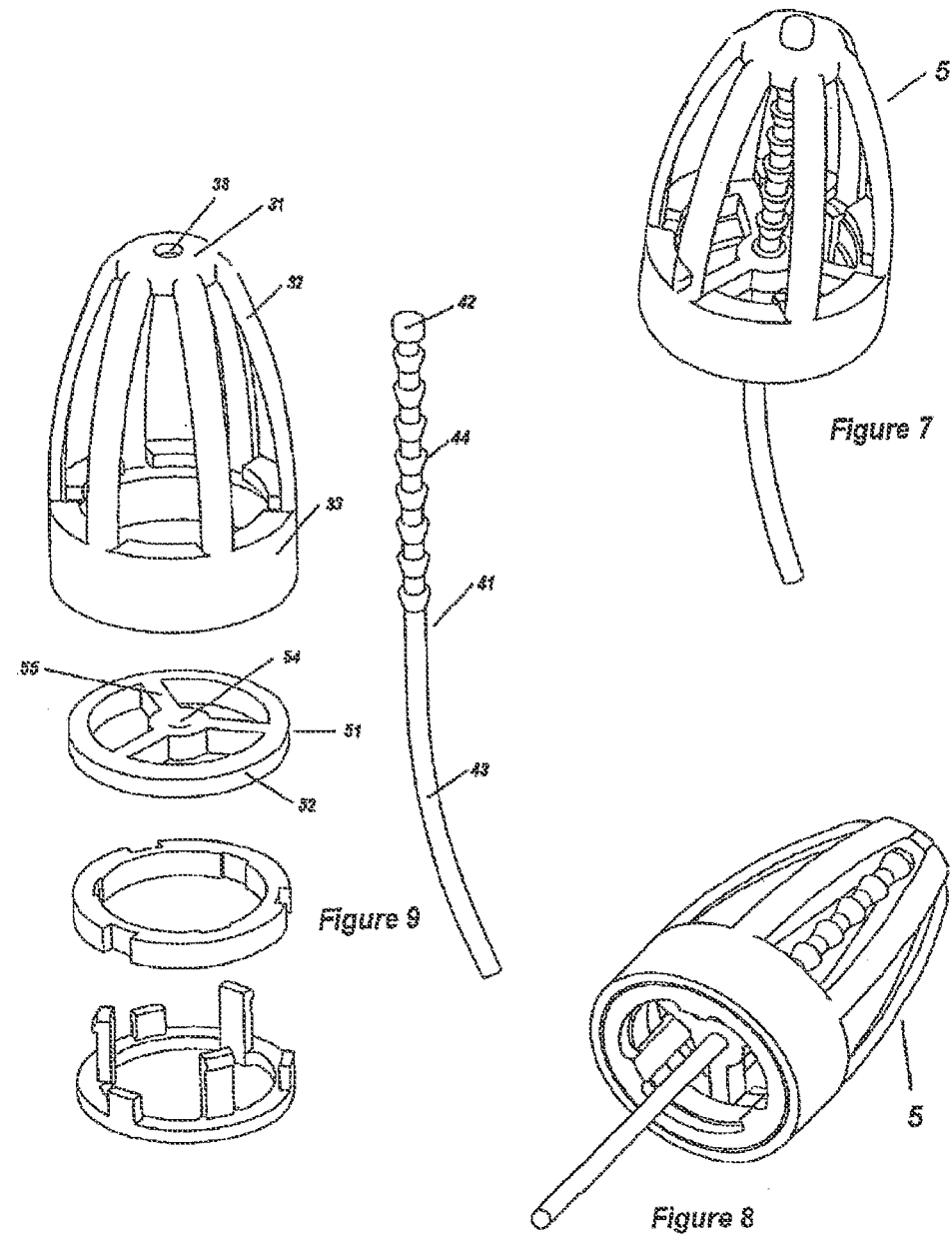

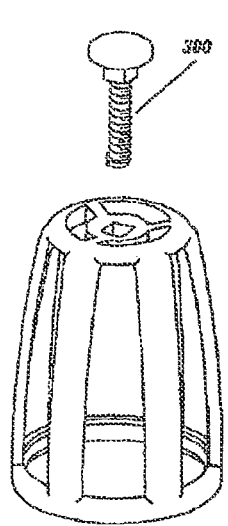
Figure 12
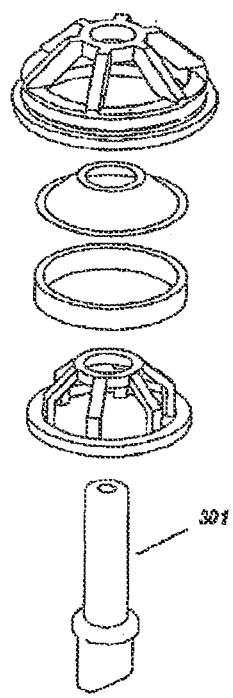
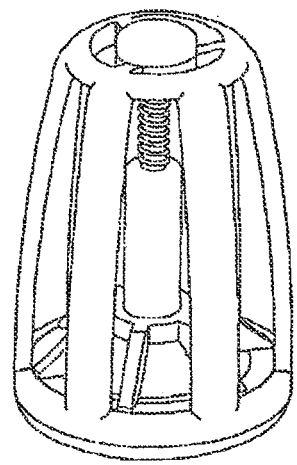
Figure 10
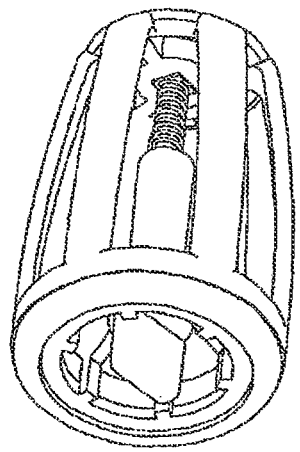
Figure 11

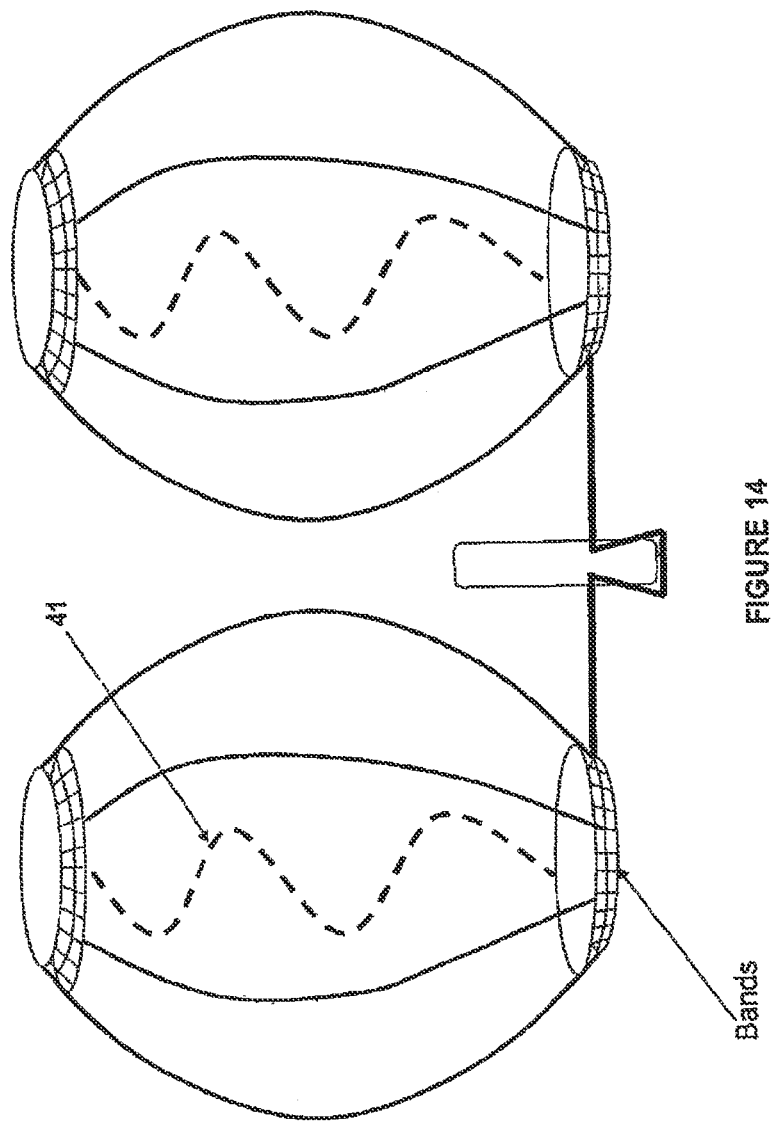

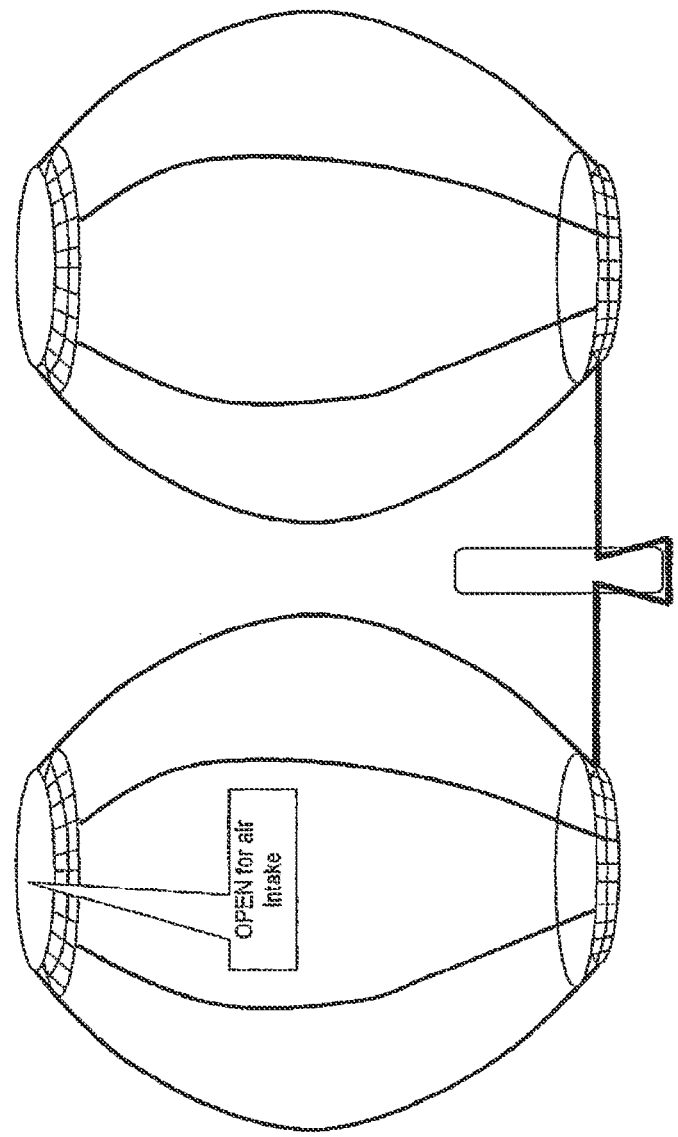

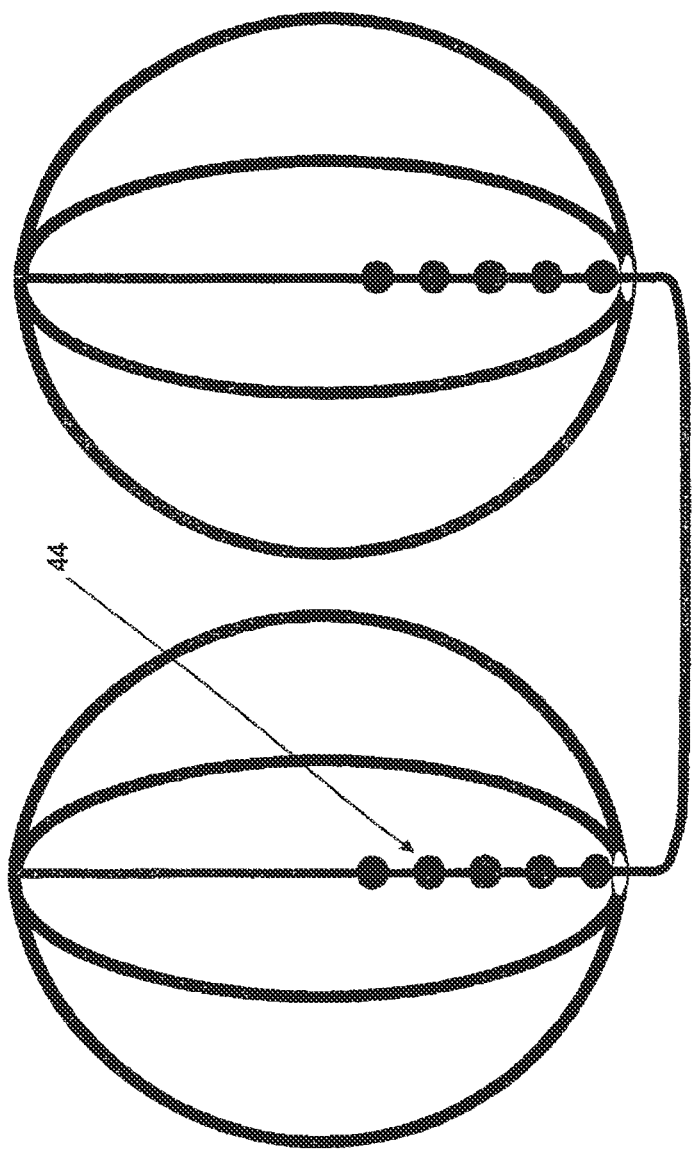

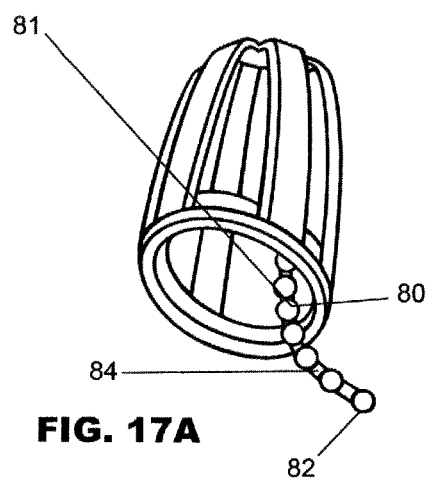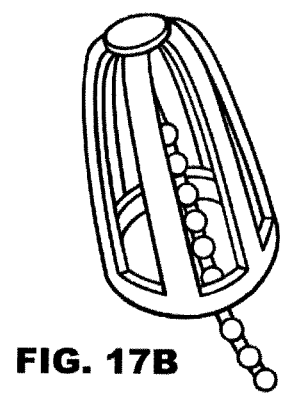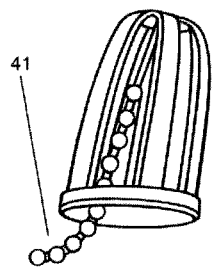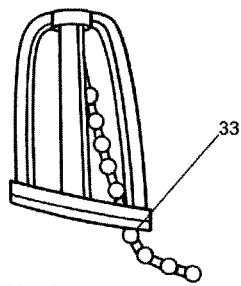
FIG. 17A
FIG. 17B
FIG. 17C
FIG. 17D

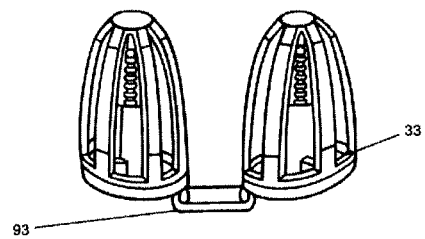
FIG. 19A
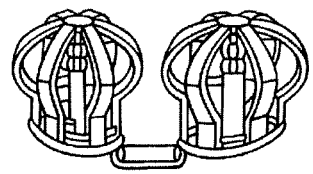
FIG. 19B
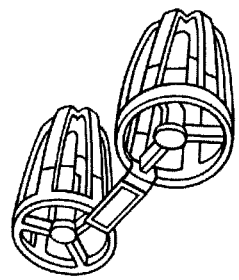
FIG. 19C

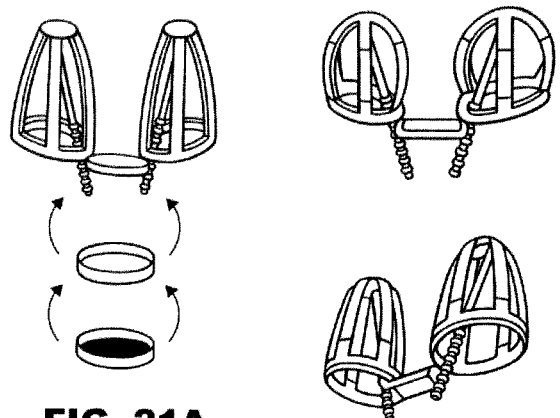
FIG. 21A
FIG. 21B
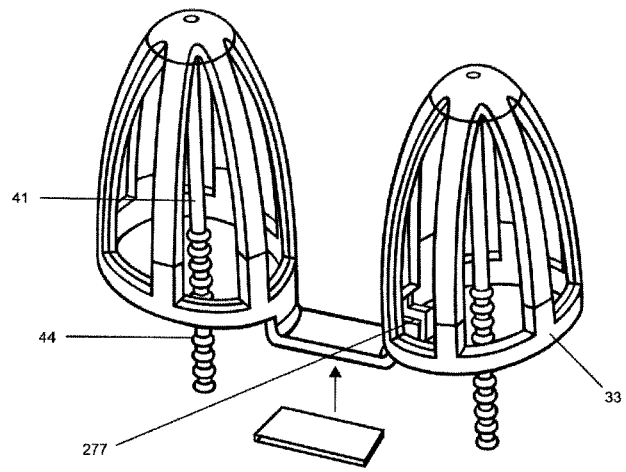
FIG. 21C

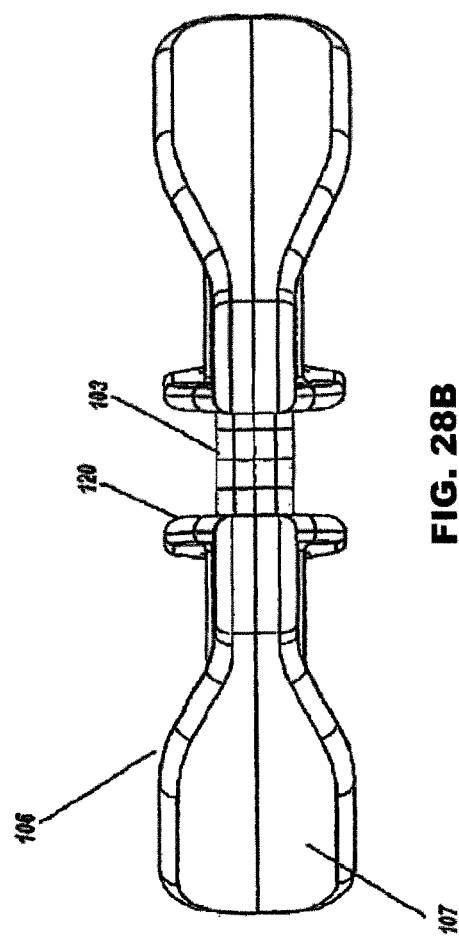

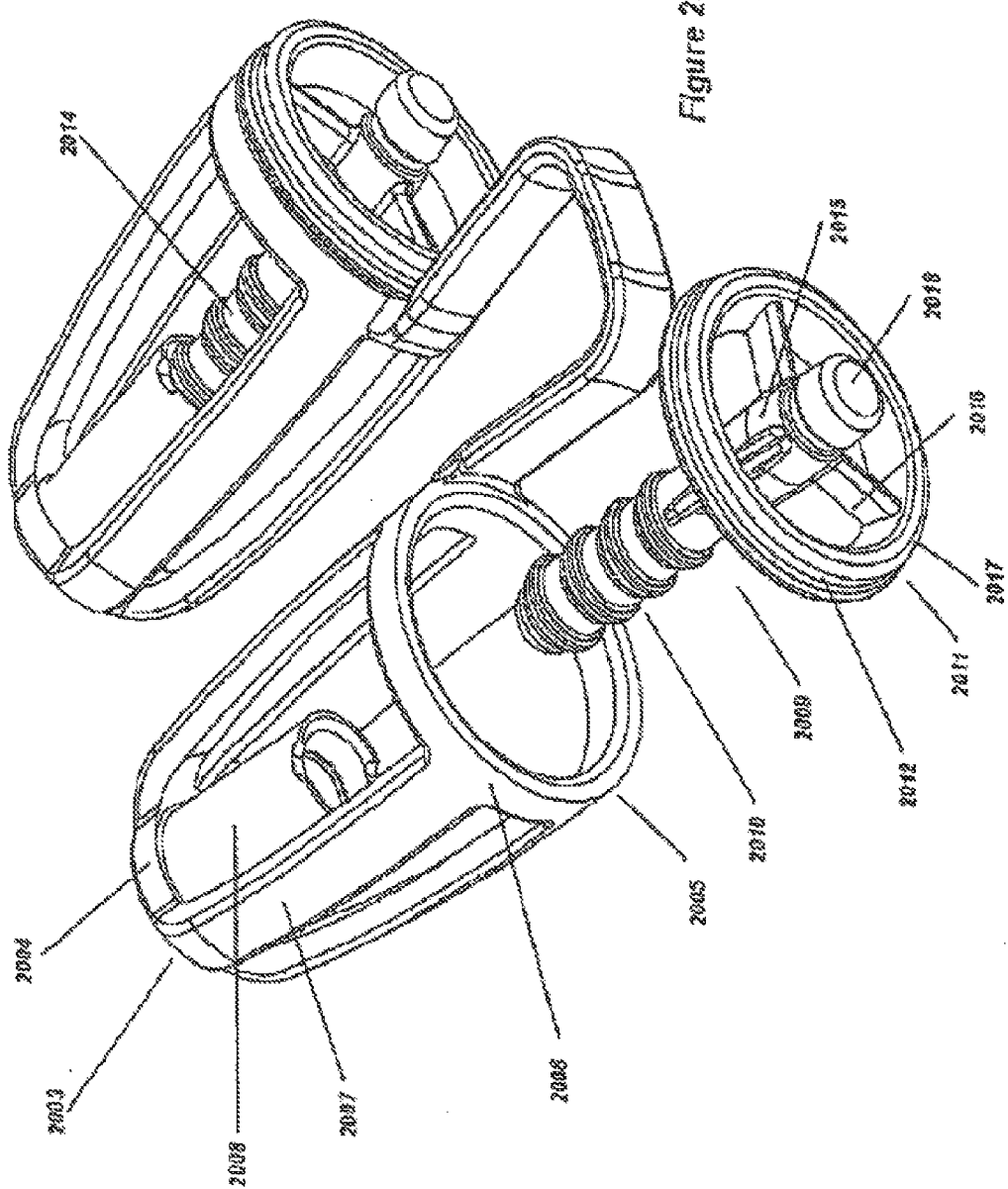

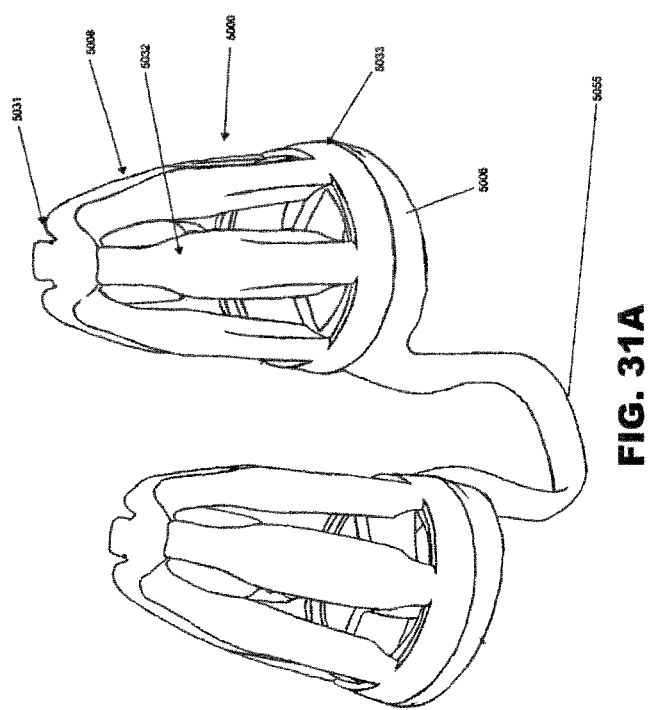

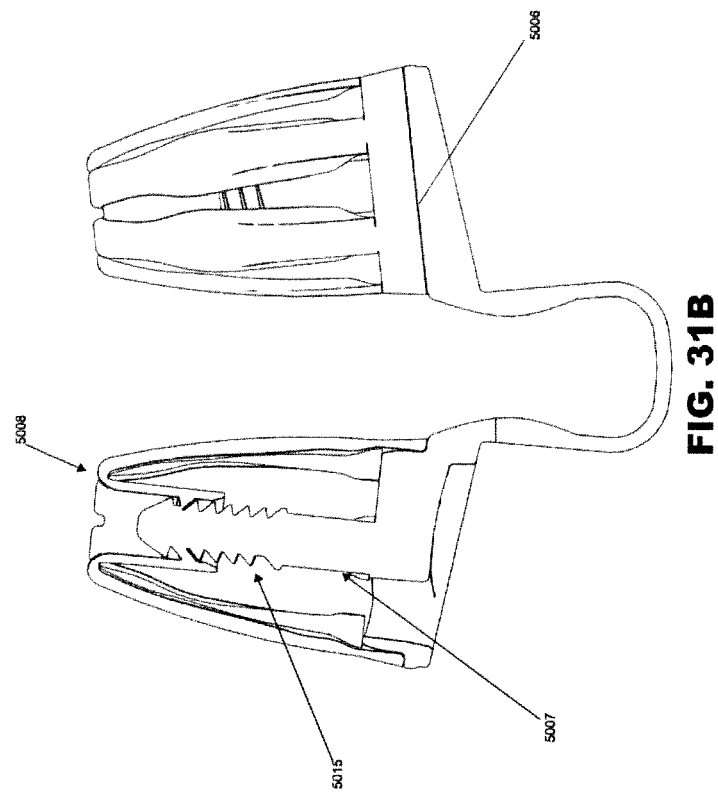

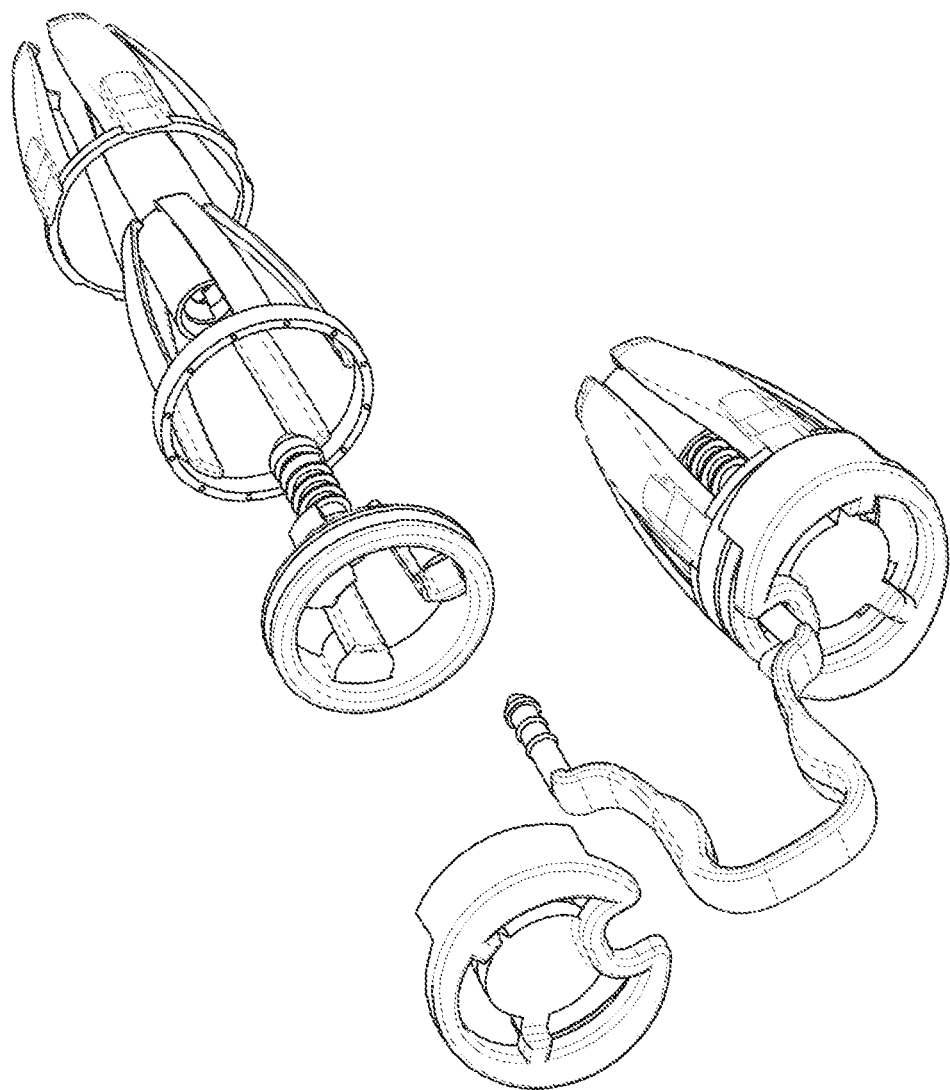

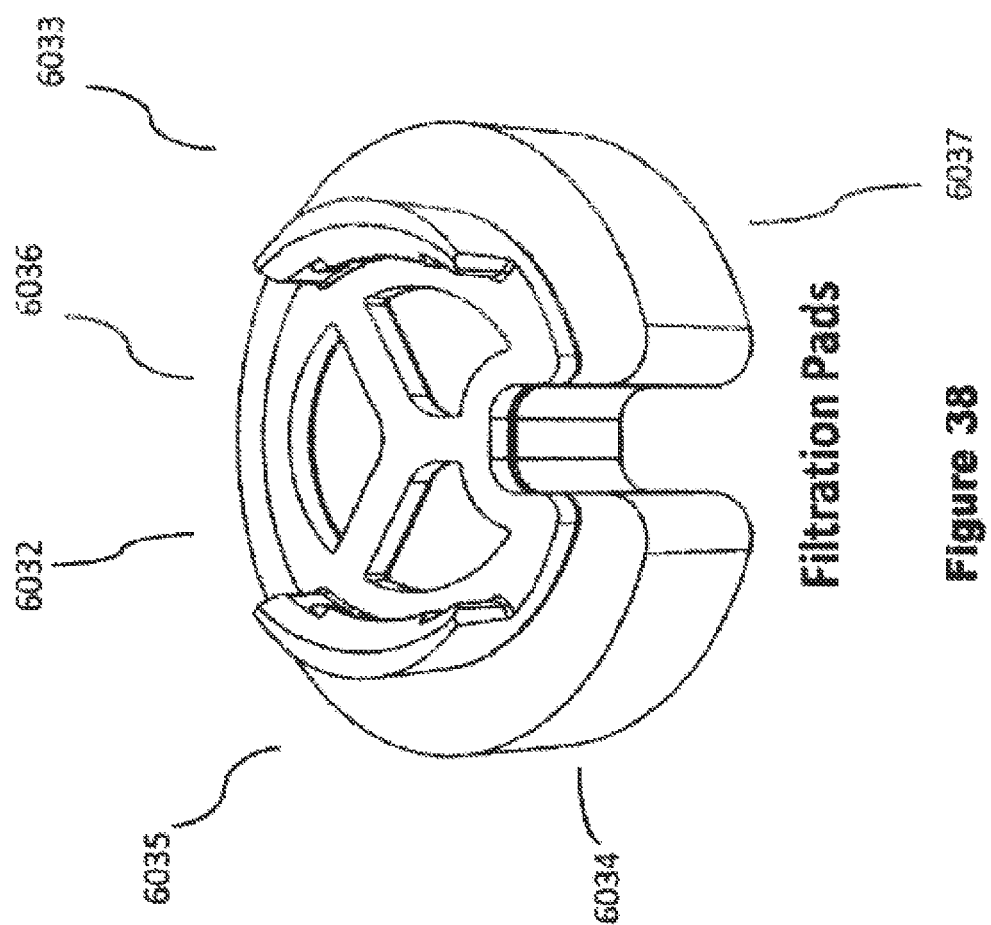

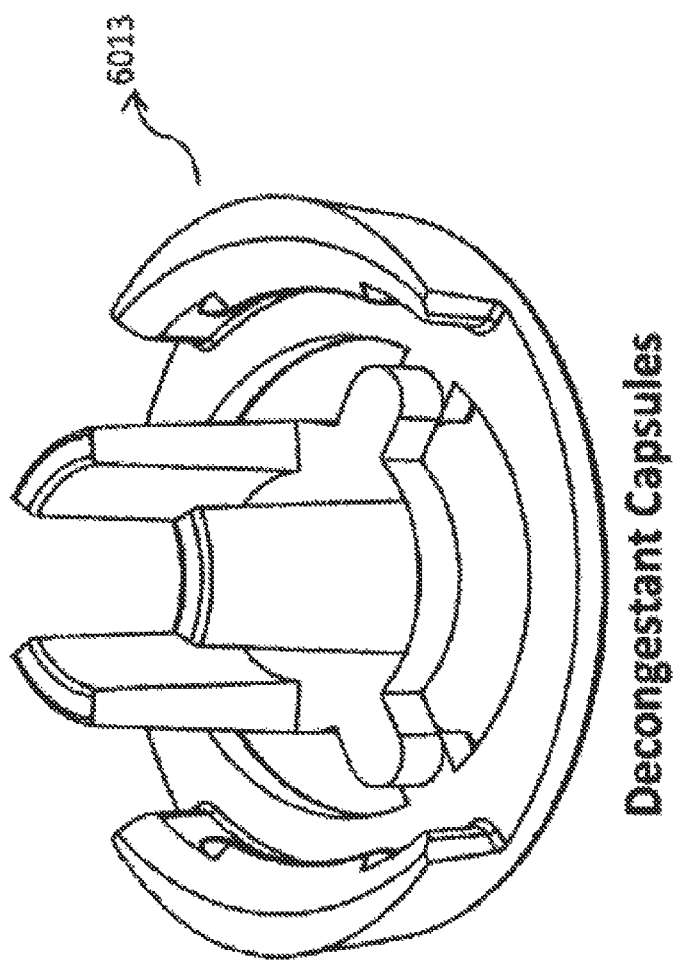
Figure 39 Decongestant Capsules

NASAL CAVITY DILATOR DEVICE

This application is a continuation of U.S. Ser. No. 12/154,868, filed May 28, 2008, claiming priority of Australian Application No. 2007202425, filed May 28, 2007 and a continuation-in-part of U.S. Ser. No. 11/363,884, filed Feb. 28, 2006, now U.S. Pat. No. 7,740,643, issued Jun. 22, 2010, a continuation of U.S. Ser. No. 10/631,415, filed Jul. 30, 2003, now U.S. Pat. No. 7,105,008, issued Sep. 12, 2006, a continuation-in-part of PCT International Patent Application No. PCT/AU2003/00504, filed Apr. 30, 2003, claiming priority of Australian Provisional Application Nos. 2003900315, filed Jan. 24, 2003, and 2002951517, filed Sep. 18, 2002, the entire contents of each of which are hereby incorporated herein by reference.

FIELD OF THE INVENTION

The present invention relates to an improved nasal cavity device for use in the nasal cavity of a human being to aid passage of air through the nasal cavity. More particularly the present invention relates to an improved adjustable nasal cavity device for combined passage of air and a medicament or fragrance and the like.

BACKGROUND OF THE INVENTION

Snoring and general breathing dysfunctions are common ailments that affect a significant proportion of the world's population. People who are disposed to such conditions can be subject to feelings of general tiredness, shortness of breath, fatigue, sleep deprivation, snoring, and even sleep apnoea, which can increase the risks of cardiac arrest.

Attempts have been made to address the above conditions. For instance one option available to sufferers involves a surgical procedure. Apart from requiring a sufferer to endure invasive surgery and the relatively high costs associated therewith, it is documented that surgical procedures are often temporarily successful, sufferers requiring repeated surgery to obtain ongoing relief.

Other methods of addressing snoring, related breathing difficulties and the like have included nasal sprays. One problem with ~pray formulations, however, is that they often contain steroidal or vasoconstrictor active agents that cause side effects and can lead to a chronic addiction problem or withdrawal difficulties. A further problem with spray formulations is that frequent dosing is required.

Alternatives to surgical procedures and sprays have included a range of contraptions that can be worn like a mask on the face of a sufferer to help maintain airways in an open condition. These types of devices involve complex designs that are very conspicuous on a wearer. Other types of devices that are worn externally include a resilient plaster applied over the bridge of the nose to externally expand the nostrils. A problem associated with this type of approach is that the plaster is not aesthetically pleasing, and is limited by both the inherent resiliency of the plaster and its ability to exert a sufficient outward force to expand and maintain a nostril cavity in an open condition. In addition the plaster requires painful removal that could result in the tearing of skin.

Other devices are disclosed in patent documents such as a device described in U.S. Pat. No. 5,895,409 that can be inserted within the nasal cavity. This device has a rigid structure and requires manufacturers to make different sized devices to cater for a range of cavity sizes. Also problems frequently arise in a nasal application when a wearer exhibits a deviated septum. A deviated septum is a curvature in the septum, the cartilage and bone that separates the nostrils. A curved septum often renders one nasal cavity a different shape and size to its neighbour and inhibits airflow through one side of the nose and can result in airflow blockage through one nostril. Prior art devices, of the type disclosed in U.S. Pat. No. 5,895,409 that are insertable within the nasal cavity, suffer the drawback that if one dilator of a symmetrical pair, to be inserted, is of a sufficiently small size to enter one nostril then the remaining dilator of the pair is too small to be effective in dilating the other nostril. Conversely, if one device of a symmetrical pair is sufficiently large to effectively dilate one nostril, its pair is often too large to be inserted in the other nostril. Even further, the device of U.S. Pat. No. 5,895,409 cannot be used to deliver a medicament.

A similar device is disclosed in U.S. Pat. No. 3,710,799, which describes a pair of open cages joined together by a flexible chain of inter-locked links, the cages being slightly larger than the nostrils but insertable therein so that the nose holds the cages in place. This device confers a deal of discomfort for a wearer upon insertion because the device is generally larger than the corresponding orifice in which it is to be inserted. Other devices are available that include a resilient plastic strip with widened ends. This type of device is usually bent prior to insertion to conform to a U-shape with the wide ends being inserted into the nostrils. The extent of dilation of the nostril cavity depends on the resiliency of the plastic to return to its normal configuration. These type of dilators are very uncomfortable for a wearer and the force generated by the resilient plastic often causes irritation to the inside lining of the nose not to mention that the article is conspicuous.

More recently the present applicant has developed a nasal cavity dilation device that addresses some of the aforementioned problems. The applicant's own U.S. Pat. No. 7,105,008 describes an adjustable nasal cavity device for improving flow of air through the nasal passage of a wearer.

To date no device or system has been provided which is capable of combining improved flow of air and delivering a medicament or fragrance or like material. This is likely because of the size constraints within the nasal cavity of a human. Hence, further improvement is required to address this problem.

Even further, general breathing problems can be initiated upon exposure to dusts, pollens, and pollution. Many people are predisposed to allergies, hay fever and even asthma on exposure to such environmental triggers. To date various means of minimising exposure to such triggers has included wearing of masks. Wearing of masks however is unsightly and significantly restricts flow of air into the nasal cavity.

It should be understood that any reference to prior art does not constitute an admission of common general knowledge.

Hence it is an object of the present invention to provide a device, which addresses one or more of the prior art disadvantages. A further object is to provide a means to help improve flow of air through the nasal passage of a human. A further object is to provide a means of combining flow of air with a supply of a medicament or fragrance or the like into the nasal passage of a human. An even further object is to provide a filter means which does not substantially restrict the flow of air into a human nasal cavity.

SUMMARY OF THE INVENTION

In accordance with the invention there is provided a nasal cavity device for combined flow of air through the nasal passage and a medicament or fragrance and the like, the device including:

a body for insertion within a human nasal cavity, the body being capable of deforming to exert an effective force on internal surfaces of a nasal cavity and thereby improve air flow through the nasal passage;

an expansion means for mounting the body, wherein in an operating condition the expansion means urges against the body causing the body to deform;

at least one defined air flow pathway within the device;

a releasable locking means for locking the expansion means and the body in operable engagement;

a demountable fragrance/medicament holder mounted in a portion of the expansion means wherein the fragrance holder and expansion means define a fragrance/medicament channel accessible to the air flow pathway;

wherein air entering the fragrance channel dispenses fragrance or medicament or the like from the fragrance/medicament holder into the air flow pathway.

The device in accordance with the present invention allows release of a medicament or fragrance by interaction with an air stream passing through the at least one defined airflow pathway. Medicament released by the passage of air can be absorbed into the body for a desired therapeutic effect.

The present device represents an improvement over the prior art devices because it provides a means of combining enhanced airflow through a nasal passage of a human patient with a fragrance or medicament. The fragrance/medicament holder can also be replaced or replenished to allow repeated dispensing of a fragrance or medicament of the like.

The fragrance channel can have an air inlet and air outlet to allow air flow through the channel for fragrance dispensing whereby fragrance merges with the at least one defined air flow pathways within the device.

The fragrance holder can be mounted in a central portion of the expansion means to maximize airflow and fragrance dispensing.

The fragrance holder can include a central holding means with interrupted well structures to allow lateral egress of fragrance or medicament or the like and an annular mounting means with air cavities therebetween to allow mounting while allowing longitudinal ingress of air flow past the central holding means.

The expansion means can include a central housing structure comprising interrupted wall members ending in a centrally located platform, which extends into the body of the device. In an assembled condition the central holding means of the fragrance holder can be received within the central housing structure, wherein the platform rests on the interrupted well structures thereby forming a roof for the central holding means.

The releasable interlocking means can include a male and female mating elements. In one embodiment the male element is mounted to the roof and extends into the body, and the female element is a oppositely disposed tubular sleeve structure extending within the body and wherein the male element is releasably received within the female element to substantially maintain the body in a desired deformed position to exert an effective force on internal surfaces of the nasal cavity walls.

One advantage of the present invention is that the central platform of the expansion means forms a roof enclosure for the central holding means of the fragrance holder and provides a support or mounting surface for the male element of the interlocking system.

The body can comprise a top frame end forming a collar and a bottom frame end forming a waistband wherein the top and bottom frame ends are interconnected by a deformable wall structure. The deformable wall structure is preferably formed from a series of spaced apart rib members. In an assembled condition the expansion means is mounted on the bottom frame end. In an operating condition the expansion means is urged by an external force against the bottom frame end causing displacement of the bottom frame end towards the top frame end whereby the flexible wall structure deforms laterally of the body to exert a force against internal surfaces of a nasal cavity wall.

Preferably the releasable interlocking means can include:

an upstanding member extending from the central platform of the expansion means, wherein when the expansion means is mounted on the bottom frame end the upstanding member is centrally located of the body, and wherein at least a part of the upstanding member includes a series of circumferential teeth;

a tubular sleeve member extending downwardly from the top frame end for receiving the upstanding member, at least a part of the sleeve including complementary internal teeth adapted to engage with the circumferential teeth; and wherein the upstanding member is received within the sleeve member upon application of an external force to one or both of the frame ends and thereafter the top and bottom frame ends are maintained at a desired distance and allowing suitable lateral deformation of the flexible ribs to exert an effective force on surfaces of the nasal cavity walls to improve passage of air therethrough.

In a related aspect of the present invention there is disclosed a nasal cavity device for combined flow of air through the nasal passage and a medicament or fragrance and the like, the device including:

a body for insertion within a human nasal cavity, the body being capable of deforming to exert an effective force on internal surfaces of a nasal cavity and thereby improve air flow through the nasal passage;

an expansion means for mounting the body, wherein in an operating condition the expansion means urges against the body causing the body to deform, the expansion means including a central housing structure comprising interrupted wall members ending in a centrally located platform which extends into the body of the device;

at least one defined air flow pathway within the device;

a releasable locking means for locking the expansion means and the body in operable engagement;

a demountable fragrance/medicament holder including central holding means comprising interrupted well structures to allow lateral egress of fragrance or medicament or the like and an annular mounting means with cavities therebetween to allow mounting to the expansion means while allowing longitudinal ingress of air flow past the central holding means, wherein in an assembled condition the central holding means of the fragrance holder is received within the central housing structure such that the platform rests on the interrupted well structures to form a roof for the central holding means thereby defining a fragrance or medicament channel for merging with the air flow pathway.

The expansion means can include a base ring structure having an inner circumferential shoulder for supporting the bottom frame end thereon and an outer concentric circumferential platform for supporting an external sheath/cage for protecting the body.

The expansion means can include a central housing comprising interrupted wall members such as a series of spaced apart legs interconnected to a central platform wherein the legs extend substantially upwardly within the body from or adjacent to edge portions of the inner circumferential shoulder. Preferably the spaced legs end in shoulder portions which each connect directly to the central platform. Preferably the edge portions include an opening therein to receive portions of a bridge structure.

The fragrance holder preferably includes a ring-like base structure being interconnected to a centrally located housing structure wherein airflow cavities are located therebetween. The centrally located housing is preferably comprised of spaced wall sections adapted to be received within the central housing of the expansion means.

The fragrance holder can also include a u-shaped recess within the ring-like base structure to accommodate an arm portion of a bridge member.

The releasable locking means can comprise of interlocking components on the top frame end and the expansion means, the interlocking components being adjustably interlockable for maintaining the top and bottom frame ends of the body at a distance effective for the wall structure to exert a desired dilating force for improving passage of air through the nasal cavity.

Preferably the releasable interlocking means can include:

an upstanding member extending from the central platform of the expansion means, wherein when the expansion means is mounted on the bottom frame the upstanding member is centrally located of the body, and wherein at least a part of the upstanding member includes a series of circumferential teeth;

a tubular sleeve member extending downwardly from the top frame end for receiving the upstanding member, at least a part of the sleeve including complementary internal teeth adapted to engage with the circumferential teeth; and wherein the upstanding member is received within the sleeve member upon application of an external force to one or both of the frame ends and thereafter the top and bottom frame ends are maintained at a desired distance and allowing suitable lateral deformation of the flexible ribs to exert an effective force on surfaces of the nasal cavity walls to improve passage of air therethrough.

Preferably the device can include an outer sheath adapted to mount over the body. The sheath comprises a circumferential bottom frame end, which in use is supported on the outer circumferential platform of the expansion means, and spaced apart ribs extending upwardly from the circumferential bottom frame end ending in curved fingers for gripping attachment at the top frame end of the body.

In one embodiment of the present invention the device can be joined to a second device by means of a bridge member whereby each device can be adjusted independently or cojointly. The bridge member includes a generally symmetric u-shaped transparent structure ending in adjustable elements. In use the adjustable elements of the bridge member are received through an opening provided in edge portions of the expansion means wherein the adjustable elements allow fine adjustment of the position of the bridge member. The fragrance holder preferably provides a recess in the base ring structure so that when the fragrance holder is mounted to the expansion means the recess accommodates a portion of the bridge member.

In a related aspect of the present invention there is disclosed a method of delivering a medicament to the nasal cavity of a human being including:

providing a device having:

a body having a top frame end forming a collar and bottom frame end forming a waistband, the top and bottom frame ends being interconnected by a series of spaced apart flexible ribs, wherein the ribs deform laterally of the body with a change in distance between the frame ends, an expansion means including a base ring structure having at least an inner circumferential shoulder for mounting to the waistband, wherein in an operating condition the circumferential shoulder urges against the waistband to initiate displacement of the waistband relative to the collar, the expansion means further including a central mounting portion formed of interrupted wall members ending in a central platform;

at least one air flow pathway within the device;

a releasable interlocking means for locking the expansion means and the body in adjustable operating engagement;

a fragrance holder including mounting means for mounting on the expansion means, wherein the fragrance holder includes a central holder for mounting within the central mounting portion of the expansion means such that the central platform forms a roof for the central holder and wherein the fragrance holder and the expansion means define a fragrance channel accessible to the air flow pathway;

the method including inserting the device within a nasal cavity of a human, manipulating the expansion means so that it is urged against the waistband, wherein the flexible ribs expand laterally against inner surfaces of a nasal cavity wall to allow substantially improved air flow through the nasal passage.

The body can be adjusted in situ or externally of the nasal cavity by a wearer to tailor a desirable degree of lateral expansion against inner surfaces of the nasal cavity walls. Hence air flow can be improved by suitable adjustment of the device by the wearer until the wall structure exerts a selectable desired dilating force against surfaces of the nasal cavity walls. Unlike any prior art device the instant device enables controlled adjustability. Even further, the device provides an airflow pathway, which is accessible to a fragrance or medicament channel to initiate dispensing of a fragrance or medicament so that it merges with the airflow pathway.

In a related aspect of the present invention there is disclosed a nasal cavity device for combined flow of air through the nasal passage and filtering air, the device including:

a body for insertion within a human nasal cavity, the body being capable of deforming to exert an effective force on internal surfaces of a nasal cavity and thereby improve air flow through the nasal passage;

an expansion means for mounting the body, wherein in an operating condition the expansion means urges against the body causing the body to deform;

at least one defined air flow pathway within the device;

a releasable locking means for locking the expansion means and the body in operable engagement;

a demountable filter holder mounted to a portion of the expansion means wherein the filter holder receives a filter member in a seated arrangement adjacent the nasal cavity opening, whereby air entering the at least one defined pathway passes through the filter member and wherein deformation of the body is sufficient to exert an effective opening force on the nasal cavity walls to substantially minimize airflow restriction.

Generally it is accepted that an air filter device worn by a human will have the effect of reducing exposure to environmental allergy triggers but at the same time reduce the flow of air. The present device provides a means of expanding the nasal cavity to allow improved airflow through the nasal passage of a human. Without being bound by any theory, the nasal cavity expansion provided by the present device substantially minimizes airflow resistance otherwise posed by the filter member.

The filter holder can include a circular base and arcuate mount portions adapted to engage receiving portions within the expansion means. The filter member can include a substantially circular pad, the diameter of which is sized to abut wall surfaces of the nasal cavity. The filter holder can further include radial arms and a semi-circular recess for receiving at least a portion of a bridging member.

In a related aspect of the present invention there is disclosed a controllably adjustable nasal cavity dilation device including:

a body having a top and bottom frame ends interconnected by a flexible wall structure, the body being shaped to enable insertion of the device within the cavity, wherein the flexible wall structure has a geometry which changes with a change in distance between the top and bottom frame ends as; and a releasable holding means adapted to maintain the top and bottom frame ends at a desired distance when in a holding condition such that the geometry of the wall structure is effective to substantially increase air flow through the nasal passage, wherein when the holding means is in a non-holding condition the distance between the top and bottom frame ends are adjustable by application or release of an external force to the body thereby producing a change in the geometry of the flexible wall structure.

The geometry of the flexible wall structure preferably describes a substantially arcuate pathway, the extent of curvature being proportional to the distance between the top and bottom frame ends, wherein the holding means retains the wall structure in a desired arcuate geometry in the holding condition and enables re-positioning of the wall structure by further application or release of the force when the holding means is released from the holding condition.

The wall structure of the device can be a series of spaced apart elongate rib members. The series of ribs each describe an arcuate pathway from the top frame end to the bottom frame end. This accentuates the disposition of the walls/ribs to extend outwardly when the respective ends of the body of the device are subjected to a compressive force exerted by the expansion means. Alternatively the flexible wall structure can be formed by a series of slits in an otherwise continuous structure.

The releasable holding means can include a locking system which assists to maintain the relative positions of the top and bottom frame ends such that the flexible wall structure is retained in an adjustably desired geometry for improving passage of air through the nasal cavity. An advantage of the holding means is that the geometry of the device can be maintained in an adjusted configuration to enable improved airflow that suits a wearer's individual requirements. Hence the amount of adjustability of the device can be controlled by the wearer.

The holding means in one such lockable form can be irreversible such as known on security ties or be unlockable. A substantial benefit in the reversible locking of the holding means is its use in changing the dimensions of the structure when the user has a different condition and the nasal cavity size has changed or where a user over-expands the device prior to insertion; the holding means allows for further fine adjustment. Such a condition can occur due to inflamed sinuses or because of colds, influenza and other nose affecting ailments or due to physical damage such as sunburnt noses, broken or damaged noses. Although it also allows use by different users this is an unlikely event for hygiene reasons.

The holding means can be a setting means where a material piece is able to hold a selected position by its nature or after being treated such as heat treated in that position. This can include metallic means, which have a degree of flexibility but retain the position after being flexed. Another means is heat settable plastics such that after selection of the correct size the item is set by insertion in hot water or otherwise.

The locking system can consist of interlocking components on the top and bottom frame ends, the interlocking components being adjustably interlockable for maintaining the frame ends at a distance effective for the wall structure to exert a desired dilating force for improving passage of air through the nasal cavity.

The interlockable components can include:

a holding base frame mountable on the bottom frame end, the base frame having an upstanding member centrally located of the flexible wall structure when the base frame is mounted on the bottom frame, wherein at least a part of the upstanding member includes a series of circumferential teeth;

a tubular sleeve member extending downwardly from the top frame end for receiving the upstanding member, at least a part of the sleeve including complementary internal teeth adapted to engage with the circumferential teeth, wherein the upstanding member is received within the sleeve member upon application of an external force to one or both of the frame ends and thereafter the top and bottom frame ends are maintained at a desired distance and allowing sizing of the flexible wall to exert a dilation force on the nasal cavity walls.

The external force applied to the device to cause expansion of the flexible wall structure can be a rotational force or a linear force to urge displacement of the top and/or bottom frame ends away from or towards each other.

The holding base structure can include a suspension platform interconnected thereto for housing a medicament such as menthol wherein the suspension platform extends within the body of the device so that the medicament is suspended out of direct surface contact with wall surfaces of the nasal cavity.

The device can comprise two bodies for simultaneous insertion within adjacent nasal cavities, the bodies being interconnected by a linking member to form a symmetrical or asymmetrical pair.

The linking member is able to interconnect the two bodies by attachment to the holding base structures or by joining the flexible wall structures of the two bodies. An advantage of the dual system is that the two bodies can be independently and controllably adjusted to suit respective nasal cavities since a wearer may want to dilate one of the pair. The linking member can join the two structures together for ease of use and as a safety measure to avoid over insertion. The link means also acts as a safety mechanism to prevent accidental inhalation. In a further variation the link means can also act as the compression means.

The nasal cavity dilation device can further including a compression means engaging with the flexible wall structure wherein when the holding means is in a non-holding condition, application or release of a force on the compression means causes the flexible wall structure to move laterally with respect to the body to describe an arcuate pathway. The device can be adjusted by applying a force to the compression means to provide a choice of one of a plurality of second dilated geometries such that the user can select an appropriate size relative to the user's nasal cavity and the holding means can maintain the selected size.

The top and bottom frame ends of the device can be substantially circular or elliptical in cross-section having openings therein, such that the top frame end has a smaller circumferential opening than the bottom frame end.

The bottom frame end can include an angled surface to suit the angle between the septum and adjacent wall of a nostril cavity to be substantially hidden from an observers view. The advantage of having an angled bottom end enables the device to be better hidden from an observers view.

In a further related aspect of the present invention there is disclosed a nasal dilation device for improving air flow through a nasal cavity including:

a first deformable body; the first deformable body having an uppermost substantially circular open end forming a collar and a lowermost substantially circular open end forming a waistband;

a series of spaced ribs connecting between the uppermost and lowermost ends, the body including a central member mounted on the collar and extending longitudinally within the body towards the lowermost end;

a holding base having a central leg mounted thereon, which leg is able to extend into the first deformable body with the holding base engaging the waistband of the first deformable body:

the leg of the holding base and the central member of the first deformable body having complementary engagement means allowing engagement which causes the holding base to act against the waistband in response to an external force so that the ribs are deflected outwardly of the body to a desired size for dilating the nasal cavity.

The first deformable body is preferably hollow and the leg of the holding base includes a series of spaced apart circumferential protrusions of external diameter equal to or greater than the internal diameter of the hollow central member.

The ribs are extendable in a direction outwardly relative to the body as the leg of the holding base progressively enters the hollow member for allowing the extent of desired dilation of a nasal cavity to be controlled.

The holding base can include a central platform on which the leg is mounted and extends upwardly towards the central member. The holding base can further include a locking ring interconnected to the platform by a series of radial arms, the locking ring including an annular shoulder that abuts the waistband when the leg engages within the central member.

The central member of the first deformable body is preferably hollow and contains a series of internal teeth and wherein the leg of the holding base can include a series of mating teeth adapted to releasably engage with said internal teeth of the central member. Alternatively the central member of the first deformable body is preferably hollow and contains an internal screw thread that mates with an external threaded section on the leg of the holding.

The holding base can also include a recessed protrusion for receiving a vapor delivery system. The advantage of the delivery of medicated vapour by the present device is that any substance such as 'Vapor Rub' can be held away from contact with the skin while allowing inhalation of medicated vapour. Hence the substance is able to function purely as a vapour for inhalation while substantially eliminating irritation that can otherwise be caused by direct contact with the skin.

The device can further include a filter. The filter can reduce the amount of airborne irritants that can otherwise infiltrate the bronchial system and cause an allergic reaction. While the filter may cause some restriction in the flow of air, any restriction is offset by the expansion of a nostril as a result of the dilation device. The device of the invention is suited to any size nostril, is economic, reusable and aesthetically pleasing.

The nasal dilation device can further include a second deformable body interconnected to the first deformable body by a bridge, wherein the first and second deformable bodies are preferably substantially symmetrical about a longitudinal axis extending centrally of the bridge.

In yet a further related aspect of the present invention there is described a nasal dilation device for improving air flow through a nasal cavity including:

a first adjustable body and a second adjustable body interconnected by a bridge, the first and second body being substantially symmetrical about a longitudinal axis extending centrally of the bridge;

each of the first and second bodies having an uppermost end forming a collar and a lowermost end forming a waistband greater in diameter than the collar, the uppermost end and lowermost ends being interconnected by a series of spaced resilient ribs, each body further including a hollow cylindrical member extending along a longitudinal axis of each body towards the lowermost end;

the device further including a releasable holding member for each body having a base member and a central leg which is able to extend into the hollow cylindrical member, the leg including a series of spaced apart circumferential protrusions of external diameter equal to or greater than the internal diameter of the hollow cylindrical member allowing the leg to enter the hollow cylinder so that the protrusions engage the hollow cylinder and the base member engages the internal sides of the waistband or the ribs extending from the collar so that the ribs are deflected outwardly of the body to dilate the cavity to a desired size.

In still a further related aspect of the present invention there is described an adjustable nasal dilation device including:

a first deformable body having one or more ribs able to engage opposing internal sides of a nasal cavity wall when in position; and an adjustable holding member which expands the first deformable body to enlarge the nasal cavity.

The adjustable holding member can comprise two arm members which interengage from opposing sides of the first deformable body.

The adjustable nasal cavity dilation device can further include:

a second deformable body connected to the first deformable body by a substantially U-shaped bridge to form an uppermost portion and a lowermost portion, the lowermost portion being sufficiently wide to span a nasal septum; the uppermost portion ending in a rib member extending downwardly at an angle to the first and second deformable bodies respectively, the first and second deformable bodies being symmetrical about a longitudinal axis extending centrally of the lowermost portion;

each of the rib members having mounted thereto a first arm member extending inwardly, each arm member including a series of ridges separated by valleys;

the first and second deformable bodies each having mounted thereon a second resilient arm member extending oppositely the first arm member towards the rib members, which second resilient arm members include a recess proximal to each end for engaging with a valley between adjacent spaced ridges on a first arm member so that the angle between the rib members and the first and second deformable body is reversibly adjusted by urging the ridges over the recess.

The first and second deformable bodies can further include a third arm member mounted thereon extending outwardly towards respective rib members, each of the third arm members being disposed above the second opposing arm members, each of the third arm members having a protrusion extending below the level of each arm, which protrusion acts as a guide to assist engagement between the first arm members and the second opposing arm members.

The respective rib members can be expanded or contracted either internally or externally of the nasal cavity by urging the teeth against the recess until an adjacent trough engages the recess. The arm containing the recess is sufficiently resilient to enable teeth members to deflect the arm downwards as the teeth act against the recess.

The rib members can include an enlarged surface area that makes contact with nasal cavity walls. This improves comfort of a wearer given that a larger surface area is in contact with surfaces of the nasal cavity walls.

The first and second deformable bodies can include symmetrical enlarged portions that are convergent to make contact with internal surfaces of the nasal cavity. The lowermost portion of the U-shaped body can include oppositely disposed contact members adapted to help retain the device in the nasal cavity by contacting lower portions of the nasal cavity.

In a further embodiment of the present invention there is disclosed a nasal cavity dilation device for improving flow of air through a nasal cavity including:

an elongate U-shape body having an uppermost and lowermost portion, the lowermost portion being sufficiently wide to span a nasal septum;

a pair of oppositely disposed adjustable rib members interconnected to the uppermost portion of the body by an arcuate portion, the each rib member extending downwardly at an angle to the body which angle is independently adjustable by application of a force thereto; and an adjustable holding means for each rib member including a system of interlocking components on the body and the wing member, the interlocking components being adjustably interlockable to allow holding and re-positioning of each rib member independent of the other to allow optimization of air flow through the nasal passage of air therethrough.

The arcuate section(s) connecting the rib members to the body can be a living hinge.

In a further related aspect of the present invention there is disclosed a method of improving passage of air through a nasal cavity including providing a variable geometry device shaped for insertion within the nasal cavity; inserting the device within the nasal cavity and adjusting the device to a desired geometry effective to apply a dilating force on internal surfaces of the nasal cavity walls for improving passage of air/fluid therethrough and adjustably retaining the device in the desired geometry.

In a further embodiment of the present invention there is disclosed a nasal dilation device for improving air flow through a nasal cavity including: a first deformable body and an adjustment member;

the first deformable body having an uppermost substantially circular open end forming a collar and a lowermost substantially circular open end forming a waistband; a series of spaced ribs connecting between the uppermost and lowermost ends, the body including a central member mounted on the collar and extending longitudinally within the body towards the lowermost end;

the adjustment member being a closing compression member having a holding base and a central leg mounted thereon, which leg is able to extend into the first deformable body with the holding base engaging the waistband of the first deformable body; the leg of the holding base and the central member of the first deformable body having complementary engagement means allowing engagement which causes the holding base to act against the waistband in response to an external force so that the ribs are deflected outwardly of the body to a desired size for dilating the nasal cavity.

The central member of the first deformable body can be hollow and the leg of the holding base can include a series of spaced apart circumferential protrusions of external diameter equal to or greater than the internal diameter of the hollow central member.

The ribs are generally extendable in a direction outwardly relative to the body as the leg of the compression member progressively enters the hollow member so that the extent of desired dilation of a nasal cavity can be controlled. The holding base can include a central platform on which the leg is mounted and extends upwardly towards the central member. The holding base can further include a locking ring interconnected to the platform by a series of radial arms, the locking ring including an annular shoulder that abuts the waistband when the leg engages within the central member. The holding base can also include a recessed protrusion for receiving a vapor delivery system. The nasal dilation device can include a second deformable body interconnected to the first deformable body by a bridge, the first and second deformable bodies being substantially symmetrical about a longitudinal axis extending centrally of the bridge.

In a further alternative of the present invention there is provided a nasal cavity dilation device for improving flow of air through a nasal cavity including:

an elongate U-shape body having an uppermost and lowermost portion, the lowermost portion being sufficiently wide to span a nasal septum, the device including a pair of symmetrical wing members having arcuate sections so that the pair of wings extend downwardly at an angle to the body;

the body including first and second oppositely disposed and laterally extending resilient arm members and one of the first or second arm members having a recess adjacent its end;

each wing member having a third arm member extending inwardly towards the first and second arm members so that the third arm member is able to slot between the first and second arm members, the third arm member including a series of teeth separated by adjacent troughs which resiliently and releasably engage within the recess on the first or second arm member the angle of the wings being controlled and variable relative to the body by adjusting the engagement between the adjacent troughs and recess to dilate a nasal cavity.

The wing members can include flattened sections which rest against internal nasal cavity walls to improve a wearers level of comfort. The wings can be expanded or contracted either internally or externally of the nasal cavity by urging the teeth against the recess until an adjacent trough engages the recess. The arm containing the recess is sufficiently resilient to enable teeth members to deflect the arm downwards as the teeth act against the recess.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

In order that the invention is more readily understood embodiments will be described by way of illustration only with reference to the drawings wherein:

FIG. 1 is a top perspective view of a fully assembled device in accordance with a first embodiment of the invention.

FIG. 2 is a bottom perspective illustration of the embodiment in FIG. 1.

FIG. 3 is an exploded perspective illustration of the device of FIG. 1.

FIG. 4 is a top perspective view of a fully assembled device in accordance with a second embodiment of the invention.

FIG. 5 is a bottom perspective illustration of the embodiment in FIG. 4.

FIG. 6 is an exploded perspective illustration of the device of FIG. 4.

FIG. 7 is a top perspective view of a fully assembled device in accordance with a third embodiment of the invention.

FIG. 8 is a bottom perspective illustration of the embodiment in FIG. 7.

FIG. 9 is an exploded perspective illustration of the device of FIG. 7.

FIG. 10 is a top perspective view of a fully assembled device in accordance with a fourth embodiment of the invention.

FIG. 11 is a bottom perspective illustration of the embodiment in FIG. 10.

FIG. 12 is an exploded perspective illustration of the device of FIG. 10.

FIG. 14 is a front diagrammatic view of a fully assembled device in accordance with a sixth embodiment of the invention.

FIG. 15 is a front diagrammatic view of a fully assembled device in accordance with a seventh embodiment of the invention.

FIG. 16 is a front diagrammatic view of a fully assembled device in accordance with an eighth embodiment of the invention.

FIGS. 19A, B & C, are varying perspective views of a device in accordance with the invention in undilated form and dilated condition.

FIGS. 21 A, B & C illustrate a device according to the invention with a alternative holding mechanism.

FIG. 29 is a perspective view of an alternative embodiment of the invention in partially assembled condition.

FIGSS. 31 A, B & C illustrate a further embodiment of the present invention in perspective, in part cross-section, and schematic respectively.

FIG. 32 is a perspective view of a fully assembled device and second device in a disassembled form in accordance with a first embodiment of the invention.

Figure 33:
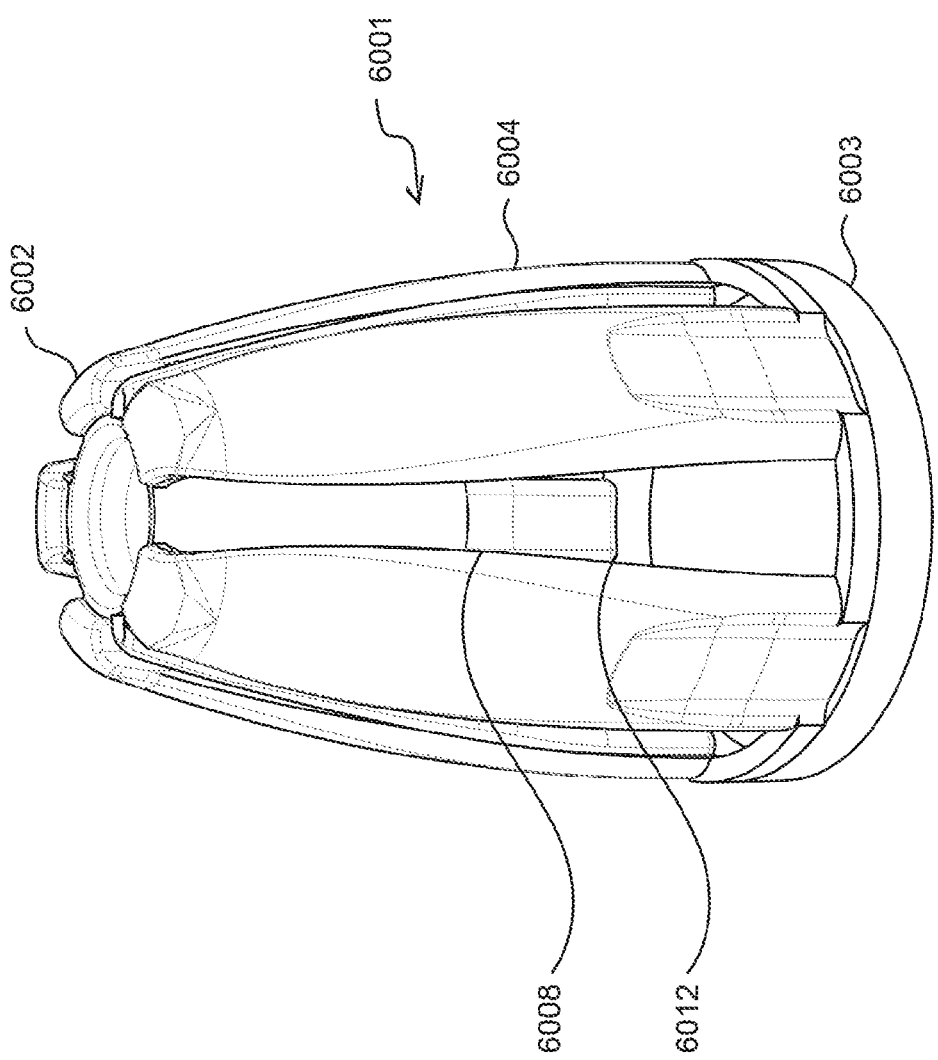

FIG. 33 is a perspective view of a body component of the device in FIG. 32.

Figure 34:
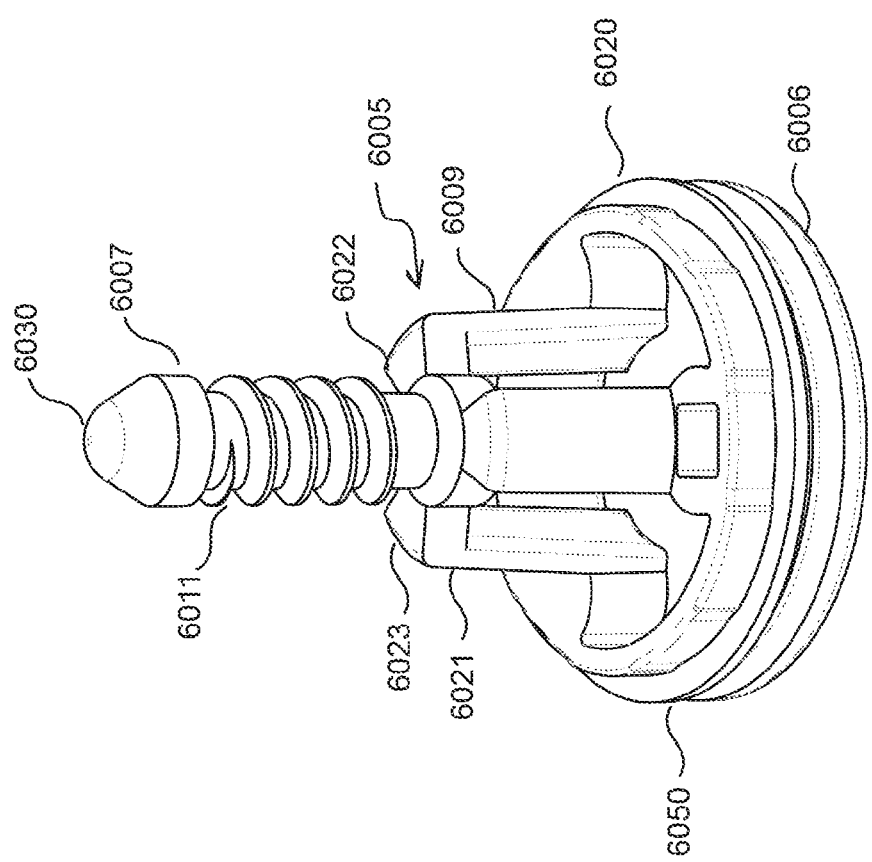

FIG. 34 is a perspective view of an expansion means of the device of FIG. 32.

Figure 35:
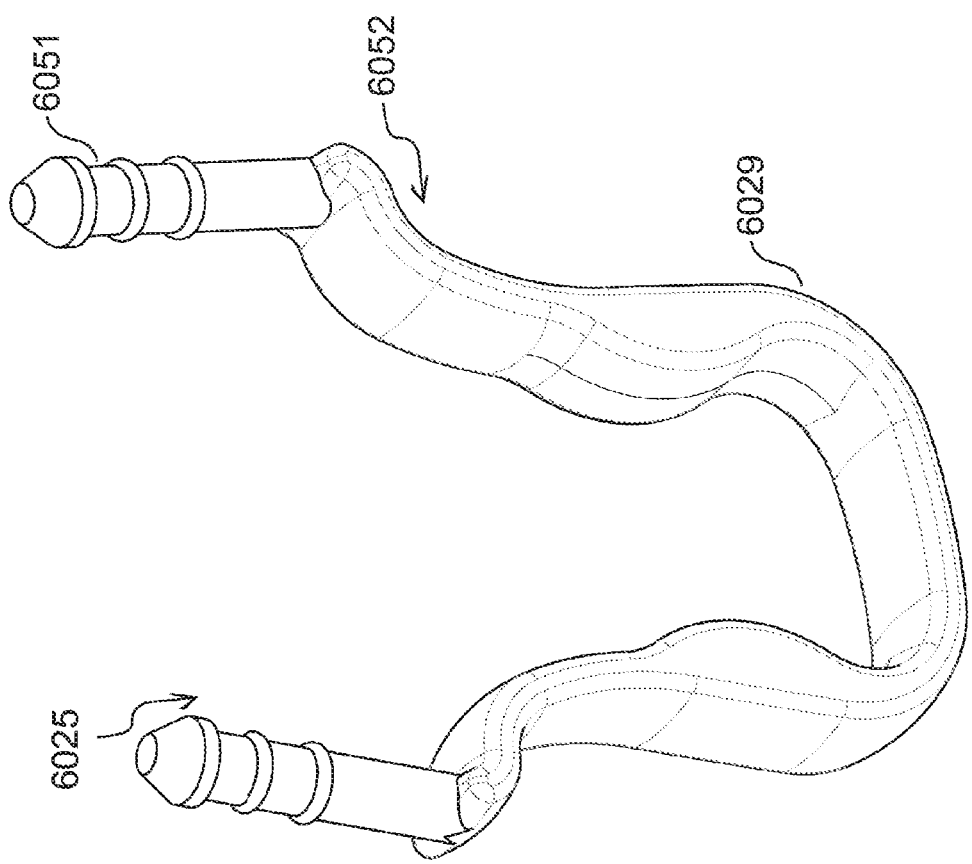

FIG. 35 is a perspective view of a bridge member in accordance with a second embodiment of the invention.

Figure 36:
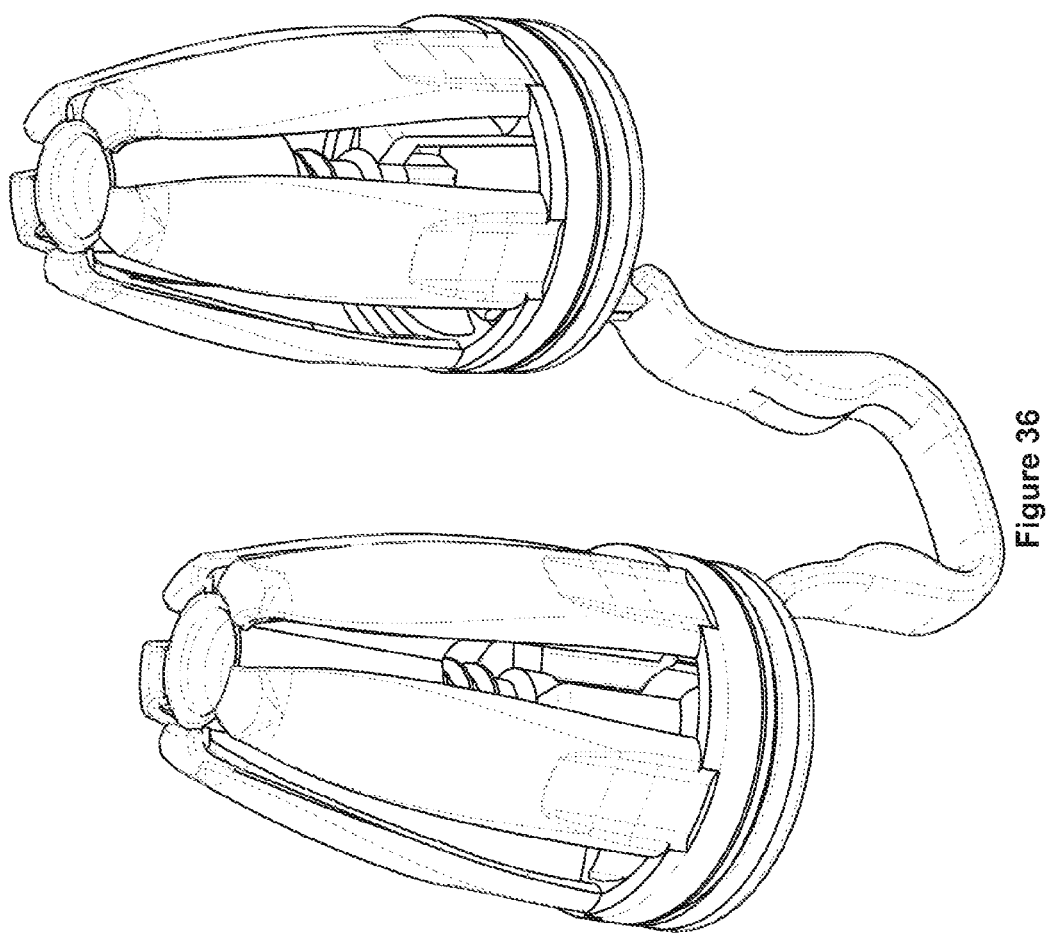

FIG. 36 is a perspective view of two devices joined by a bridging member

Figure 37:
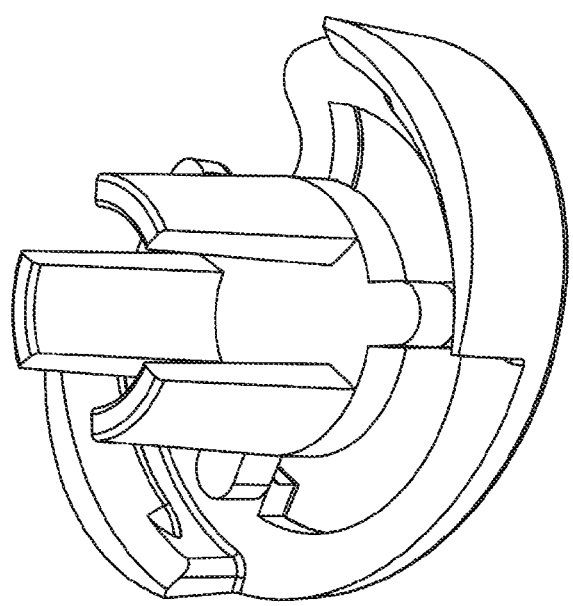

FIG. 37 is a perspective view of a fragrance/medicament holder according to the invention;

FIG. 38 is a perspective view of a demountable filter holder in accordance with a preferred embodiment of the invention;

FIG. 39 is a perspective view of a fragrance/medicament holder according to FIG. 37 including a medicament pellet.

DETAILED DESCRIPTION OF THE PREFERRED EMBODIMENT WITH REFERENCE TO THE DRAWINGS

Referring to FIGS. 1 to 5 there is shown an improved adjustable nasal dilator device (1) insertable within the nasal cavity of a human being to improve the flow of air through the nasal passage. The device includes a body (2) comprising a top (3) and bottom (4) frame ends interconnected by a series of spaced flexible ribs (5). The top and bottom frame ends are open and substantially circular, and the diameter of the bottom frame end is greater than the corresponding diameter of the top frame end to provide a body shape for convenient insertion within a nasal cavity.

The device (1) also includes a holding base member (6). As best seen in FIG. 2, the holding base member mounts the bottom frame end (4) of the body (2). The holding base member includes an inner circumferential platform (7) for supporting the bottom frame end (4) of the body (2) in a mounting position. The holding base member also includes an outer concentric circumferential platform (8) for mounting outer sheath (9).

The holding base member includes a series of mounting points (10) located in spaced relation on inner circumferential portions of the inner platform (7). The holding base member includes leg members (11) extending upwardly from the mounting points. The legs end in shoulder portions (12), which connect to a central platform (13). The legs and central platform form an internal housing structure for receiving corresponding medicament housing (14) of medicament cartridge (15).

The device further includes an interlocking system consisting of interlocking components (16), mounted to the holding base member, and mating component (17) extending inwardly of the body (2) from the top frame (3). In operation the interlockable components maintain the top (3) and bottom frame (4) ends of the body at a distance effective for the flexible ribs (5) to exert a desired dilating force for improving passage of air through the nasal cavity.

In the embodiment shown in the figures the releasable interlocking means include:

an upstanding member extending from the central platform wherein when the holding base member is mounted on the bottom frame the upstanding member is centrally located of the body, and wherein at least a part of the upstanding member includes a series of circumferential teeth;

a tubular sleeve member extending downwardly from the top frame end for receiving the upstanding member, at least a part of the sleeve including complementary internal teeth adapted to engage with the circumferential teeth; and wherein the upstanding member is received within the sleeve member upon application of an external force to one or both of the frame ends and thereafter the top and bottom frame ends are maintained at a desired distance and allowing suitable lateral deformation of the flexible ribs to exert an effective force on surfaces of the nasal cavity walls to improve passage of air therethrough.

The holding base member further includes a locking segment (14) for receiving a medicament cartridge (14) in a releasable locking engagement.

The nasal cavity dilation device is for urging the cavity towards an open/dilated condition. The device has a body (8) with a flexible wall structure formed by a plurality of longitudinally extending elongated ribs (32) extending between a top frame (31) and a bottom frame (33). The top frame (31) has an outer circular collar (35) with inner radial like struts (36) providing flow through openings (37) and a shaped opening forming a mounting opening (38). The bottom frame (33) is a circular waistband with a plurality of elongated spaced ribs (32) connected to the collar (35) and the waist band (33). The ribs at least are made from flexible plastics so that the wall structure has variable geometry. The sizing of the device is such that it is insertable within the nasal cavity.

The nasal dilation device (5) further includes a compression means comprising a connecting link (41) having a stop (42) larger in dimension than the smooth elongated chord (43) and able to be held in the mounting opening (38). The smooth elongated chord extends in position through the centre of the body (8). At or close to the top of the link (41) between the stop (42) and the smooth elongated chord (43) is a plurality of protuberances (44). In this embodiment the protuberances are spaced sawtooth structure in profile. The plurality of protuberances (44) provide a plurality of locking positions when the smooth elongated chord (43) is pulled forcing the top frame (31) closer to the bottom frame (33) and thereby deflect the elongated ribs such that the geometry of the device is adjusted by application of a force on the compression means (41) to cause the flexible wall structure to proceed from a first substantially undilated geometry to adopt a second dilated geometry (best seen in FIGS. 17H and 18B).

A holding means in the form of a holding base (51) having a bottom locking ring (52) and radial arm members (55) extending inwardly from the locking ring in a frustoconical configuration to a central platform (54) having a central shaped locking opening (58). The holding base (51) is sized to close off the bottom opening (39) of the body (8) of the device (5) by the locking ring (52) engaging the waistband (33) of the body (8). The shaped locking opening (58) is able to receive a protrusion (44) of the link (41) and thereby maintain the relative positions of the top frame (31) and the bottom frame (33) and thereby maintain the flexible wall structure (32) in a selected second dilated geometry. In the second dilating geometry the device is sized and positionable against and between the internal walls of the cavity and the septum thereby opening the cavity to enable passage of air and/or fluid therethrough.

The device further includes a frustoconical filter (62) with a central opening which is insertable in the central opening (53) of the locking ring (52) of the holding base (51). The filter (62) is held in position by a closing frame (64) similar in structure to the holding base (51) but having a central circular opening rather than a shaped locking opening (58).

It can be seen therefore that due to the framework structure of the device and in particular the framework structure of the top frame (31) the holding base (51) and the closing frame (64) and due to the porosity of the filter (62) airflow is available into the nasal cavity. The variable geometry of the wall structure including the ribs (32) is implemented by a compression means engaging with the flexible wall structure wherein the geometry of the device is adjustable by application of a force on the compression means to cause the flexible wall structure to proceed from a first substantially undilated geometry to adopt a second dilated geometry.

The filter (62) can be a material such as felt which can in turn be used to deliver medicated vapour such as that derived from "vapour rub"™. Alternatively a filtration device can be inserted within the closing frame to prevent inhalation of dust or pollens which can otherwise initiate allergic reaction by a wearer of the device.

FIGS. 4 to 9 show a nasal cavity device similar to the embodiment of FIGS. 1, 2 and 3 except that instead of having a body 8 that is substantially cylindrical, the body is pyramidal from a circular base to a top point. Another difference is the shape of the protuberances 44 on the link and thereby the change of shape of the shaped locking opening (58). However the operation is substantially identical.

In FIGS. 10 to 12 the link is formed by a screw means (300) extending through and being held by an opening in the top frame and engaging an elongated nut means (301) able to receive the screw and held by an external flange in the bottom frame. By relative twisting of the screw means and the elongated nut the top frame is brought towards the bottom frame and the flexible ribs can be deflected outwards to form a larger dilated second geometry of the required size for the nasal cavity of the user.

Figure 13:
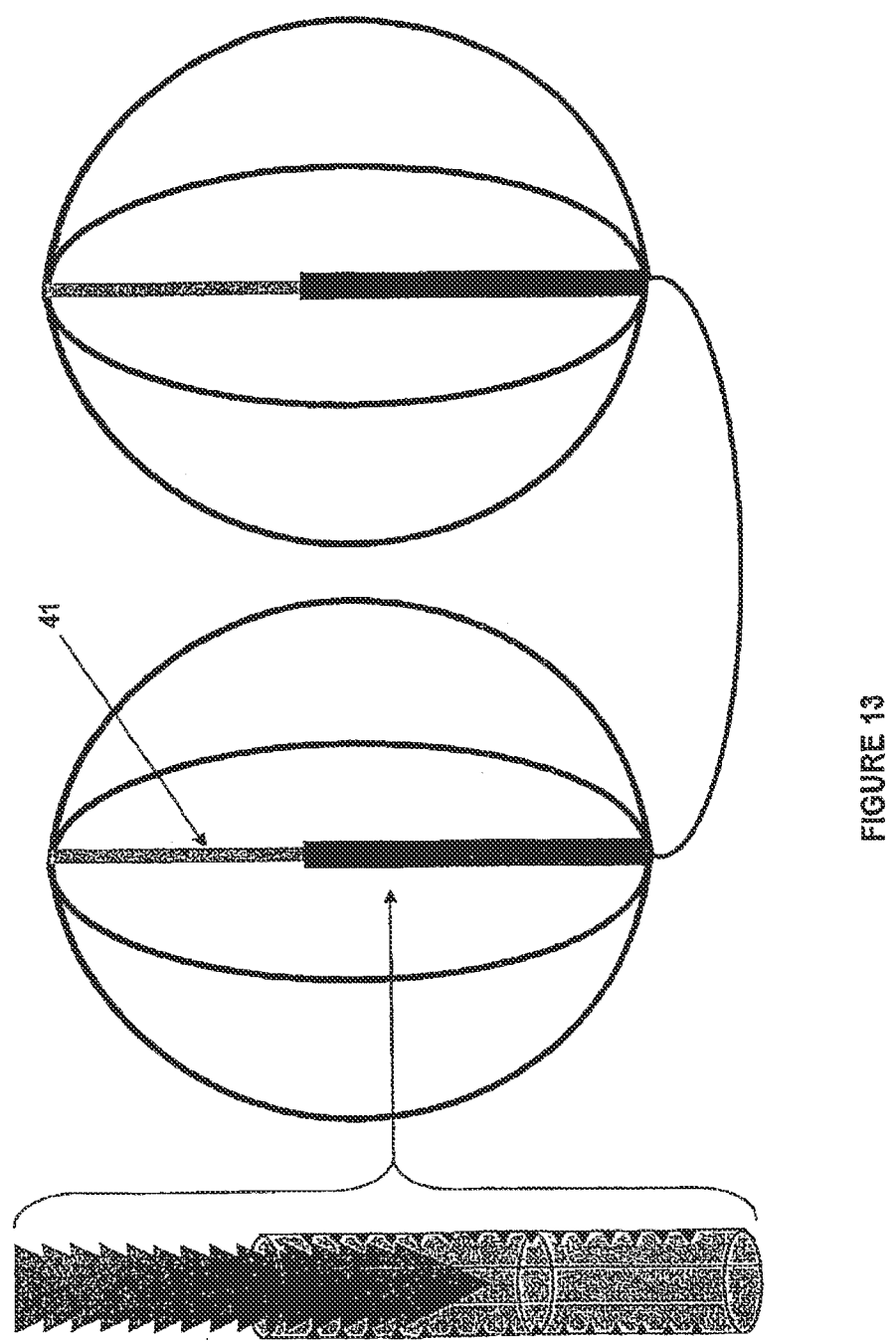
FIG. 13 is a front diagrammatic view of a fully assembled device in accordance with a fifth embodiment of the invention.

In FIGS. 13 to 16 the body structure is substantially spherical with the link (41) being formed of a sawtooth locking means in FIG. 13, a wire means in FIG. 14 that retains its position when the North and South poles of the body of the device are compressed towards each other. In FIG. 16 a plurality of circular protuberances (44) on the link are resistively engageable with an opening at the South pole of the spherical body shape.

FIGS. 17 A, B, C, D, E, F, G & H are varying perspective views of a device in accordance with a further embodiment similar to the initial embodiments. However they are shown in linked pairs for use in each nostril of the user with each link being joined by a joining member (200). In this embodiment of the invention FIGS. 17 A, B, C, D, E, F, & G show the device in a first undilated form and FIG. 17 H is in a second dilated form.

Figure 17E:
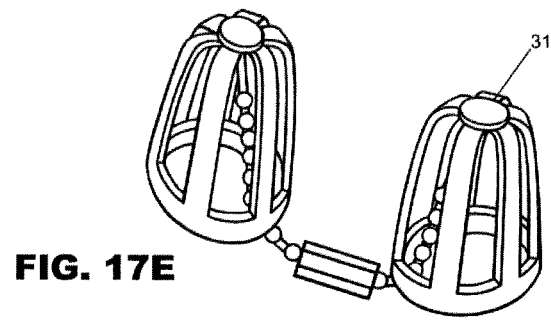
FIGS. 17 A, B, C, D, E, F, G & H are varying perspective views of a device in accordance with a ninth embodiment of the invention with FIGS. 17 A, B, C, D, E, F, & G being in a first undilated form and FIG. 17 H being in a second dilated form.
Figure 17F:
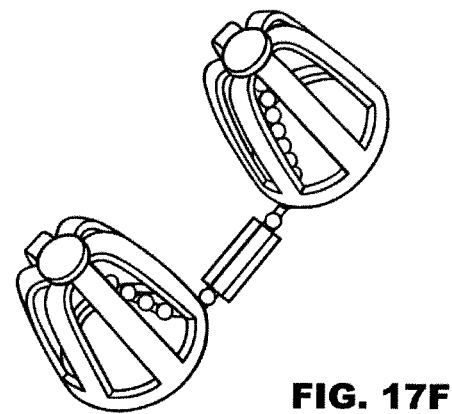
Figure 17G:
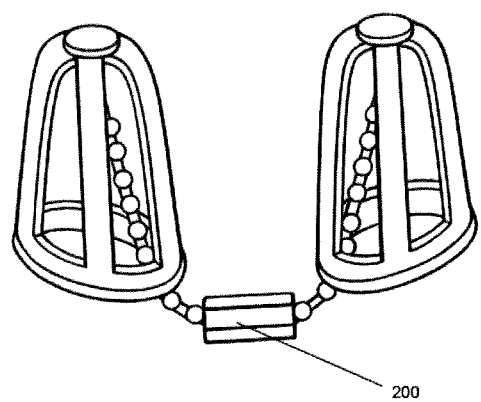
Figure 17H:
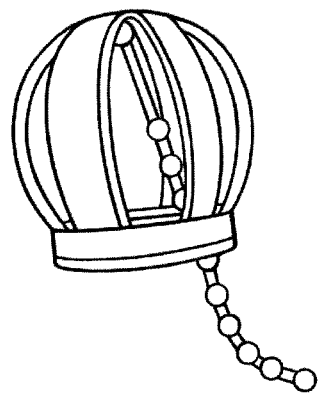

With particular reference to FIGS. 17C and D there is shown the waistband (33) of the device exhibiting an angled configuration. An advantage of the angled waistband is that some noses exhibit a lower septum relative to the internal wall of an adjacent nostril cavity so that a corresponding angled end frame on the device allows the device to be less obtrusive.

FIG. 17 C, in a perspective view, also shows an alternative holding means and compression means. In this embodiment the compression means comprises a connecting link (41) that is anchored at one end to the top frame (31) and includes an elongate chord. The chord exhibits a series of spaced apart protuberances (82) along a substantial portion of its length. The holding means comprises a resilient boss or clip (80) integral to and extending from an internal surface of the waistband (33), having an opening (81) to hold the chord. The clip is sufficiently small and resilient to enable a protuberance or even a neck portion (84) of the chord, spaced between adjacent protuberances, to enter to extend in to the opening and thereafter being held captive within the clip to maintain the elongate ribs in a desired condition. Alternatively the opening in the clip is only large enough to accommodate a length of chord between the protuberances, and once a length of chord is placed within the opening, a protuberance, being larger than the opening, rests beneath the opening to prevent the chord from being inadvertently displaced.

In an alternative embodiment (not shown) the waistband can incorporate an opening therein which serves as a holding means. In this embodiment the chord is able to be wedged tightly within the opening in the waistband and thus the chord needn't include any protuberances.

Figure 18A:
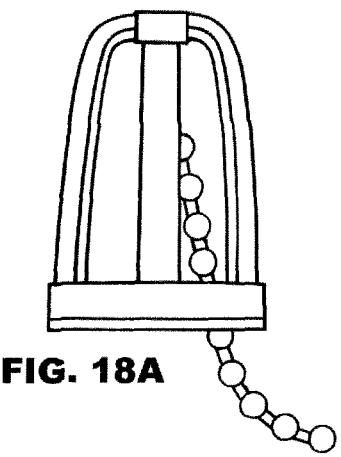
FIGS. 18 A & B, are varying perspective views of a device in accordance with a tenth embodiment of the invention with FIG. 18A being in a first undilated form and FIG. 18B being in a second dilated form.

FIGS. 18A & B also show a before use and in use position. FIG. 18A represents a first undilated form showing a substantially cylindrical body shape while FIG. 18B is in a second dilated form in a substantially sperical shape.

Figure 18B:
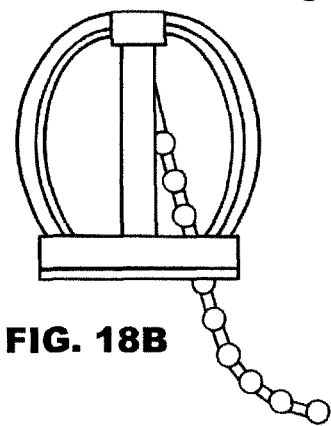

Referring to FIG. 18B there is shown a fully assembled device locked in a compressed, condition. During the operation of compression, the rib walls (32) move outwardly from the resting geometry of the device to describe an altered geometry akin to a continuous parabolic-shaped curve. In this altered geometry at least a part of the surface area of a rib wall (32) makes contact with the internal surface of the cavity. The rib walls (32) are fabricated from resilient materials such as plastics, which enable them to exert and maintain an opening pressure on the internal surface of the cavity.

Referring to FIGS. 19 A, B & C there is shown a device linked in tandem for insertion within nasal cavities one device being joined to the other by a link (93). As is shown the tandem device can include a circumferential ring (95) mountable within the opening defined by the waistband. The ring can include a material such as a felt thereon for retaining a substance capable of delivering a vapour. Alternatively the circumferential ring can include a filter (96) which can be of a desired pore size to reduce inhalation of airborne particulate matter that can otherwise initiate an allergic reaction.

Figure 20:
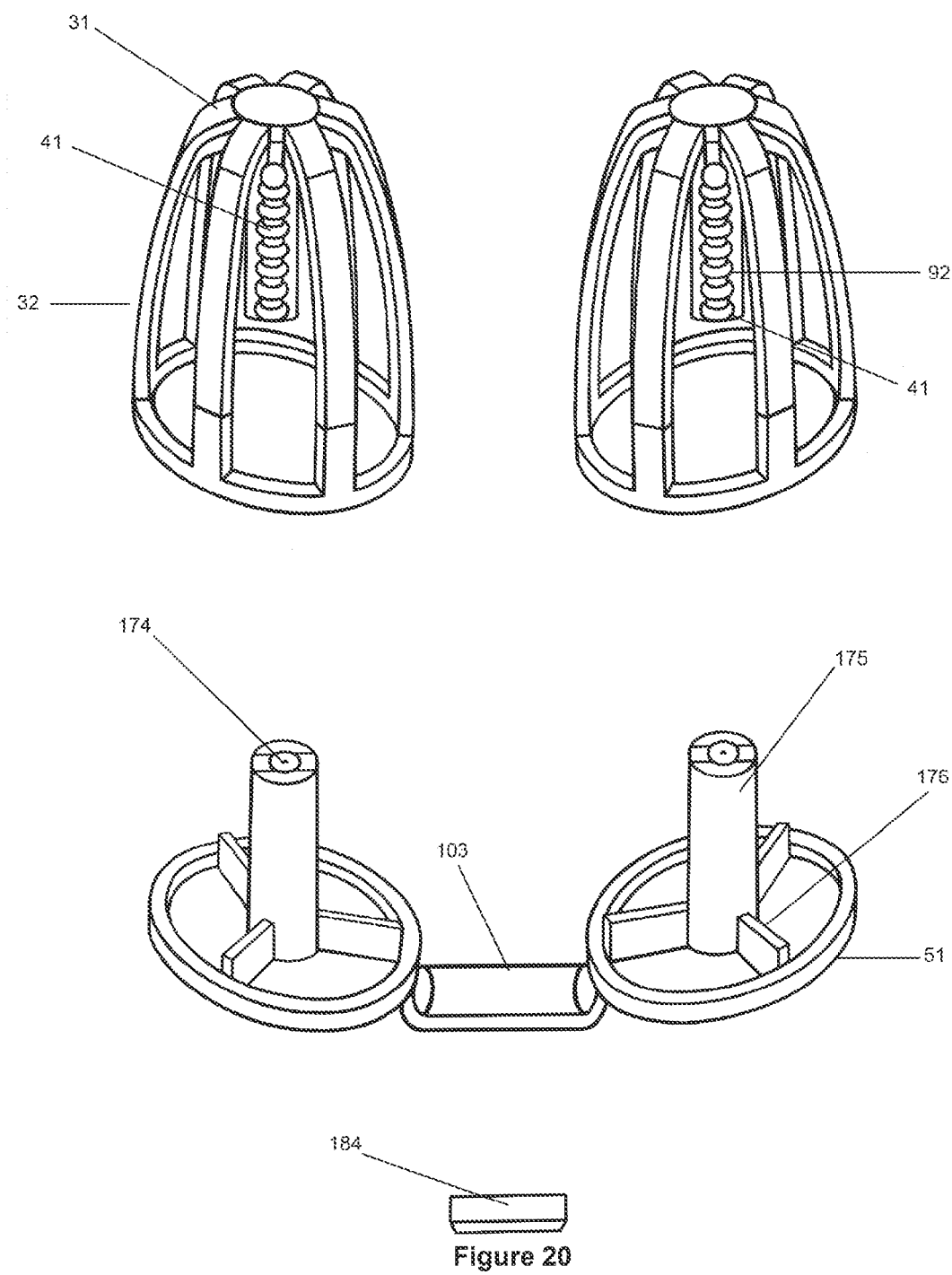
FIG. 20 is a device in accordance with the invention showing an alternative holding and expanding mechanism.

FIG. 20 shows a tandem device having an alternative compression and holding mechanism. While the principal of operation is similar to that illustrated in FIG. 12 the differences of note are that the elongate link (41) is fixed to the top frame (31) and includes a series of spaced apart protuberances (92) along a substantial part of its length. The link is held in a desired position by a holding means in the form of a holding base (51) with a centrally located upstanding base (175) supported by base cross-members (176). The upstanding base has a centrally located bore (177) with internal mating threads extending along one side of the bore for mating with the protuberances (92) on the link (41). In order to compress the adjustable ribs (32) an external pressure is applied to either the top and/or bottom frame thereby to urge the protuberances within the bore and into mating engagement with the portion of the bore that includes internal threads. To release the device from an expanded condition the bottom frame is rotated so that the protuberances disengage from the internal threads on the one side of the bore and thereafter the protuberances can freely slide to release the link from the bore. The devices are linked together by a nose bridge (103) which includes a recess for housing a vapour dispenser (104).

Referring to FIGS. 21 A, B, and C there is shown a modification to FIG. 20 wherein one part of the holding means is a clip (277) positioned on an internal surface of the waistband (33) for receiving a corresponding protuberance (44) on the link (41). FIG. 21 B shows the device in a compressed/expanded condition and a non-expanded condition. In both instances the chord is held in a position by locking a protuberance within the clip.

As shown in FIGS. 4, 5 and 6 the device has a resting-geometry in the absence of compression, for enabling easy insertion within a body cavity, although it is understood that the device can be dilated prior to insertion within a nasal cavity. The resting geometry of the structure (4) exhibits a bullet or dome type shape wherein the collar (6) exhibits a smaller relative circumference to the opposite waistband end (7) to facilitate easy insertion of the device within a cavity. In the resting geometry the device (5) is sufficiently small to enable insertion within a very wide range of cavity sizes and thereafter the geometry changes as a force is exerted on the top end of the structure by the chord (41) to urge a surface of the ribs against the nasal cavity to improve breathing and air flow within the cavity.

The applicant does not intend to limit the invention to the disclosed embodiments, and any modifications or alterations that are obvious to a person skilled in the art from this disclosure are within the scope of this invention and covered herein.

Figure 22A:
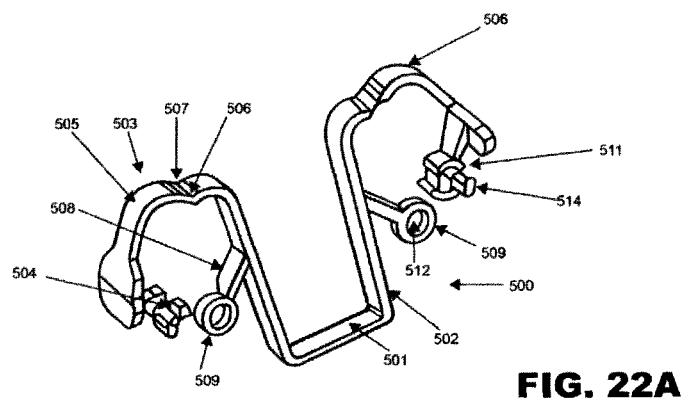
FIGS. 22 A, B & C are varying perspective views of a device in accordance with a tenth embodiment of the invention illustrating a device in an open condition.
Figure 22B:
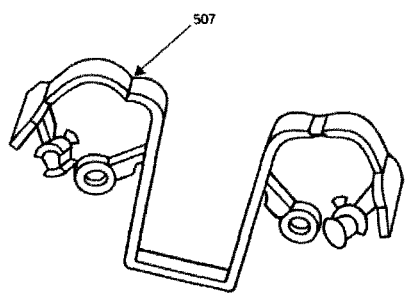
Figure 22C:
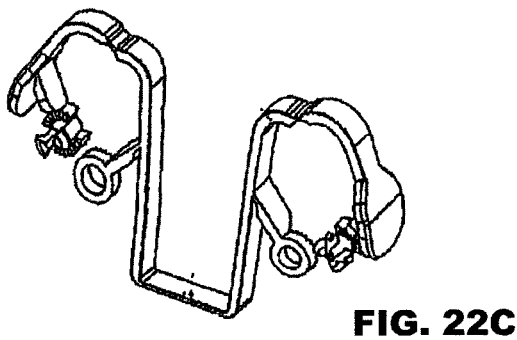
Figure 23:
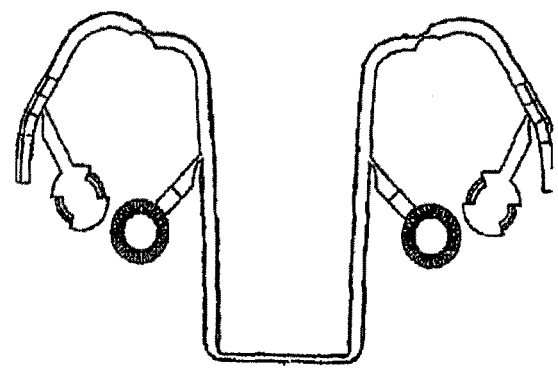
FIG. 23 is an end plan view of the embodiment shown in FIGS. 22 A, B & C in an open condition.
Figure 24A:
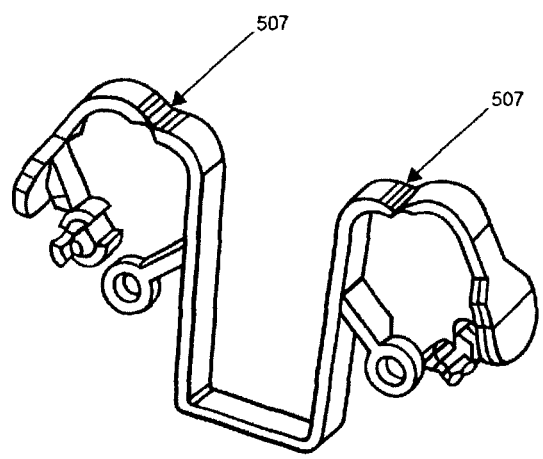
FIGS. 24 A & B are varying perspective views of a device, in accordance with a tenth embodiment of the invention, in assembled condition.
Figure 24B:
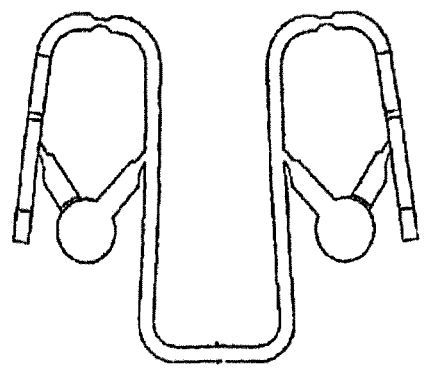
Figure 25A:
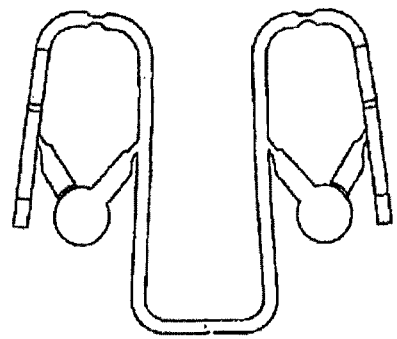
FIGS. 25 A & B are end views of the device shown in FIGS. 24 A & B.
Figure 25B:
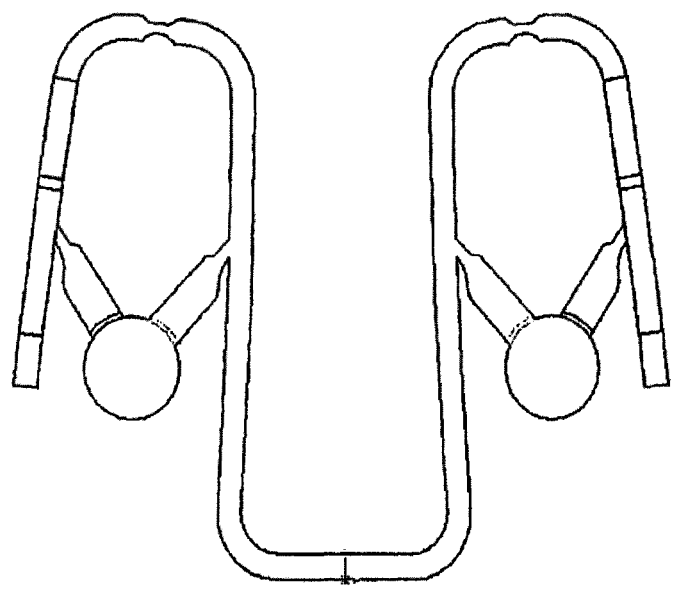
Figure 26A:
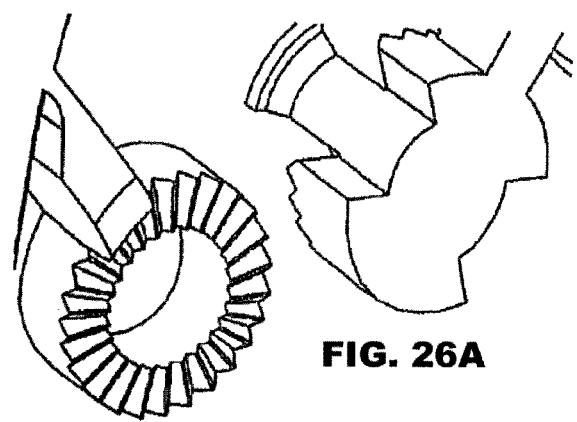
FIGS. 26 A & B are magnified perspective views of locking means exemplified in the tenth embodiment.
Figure 26B:
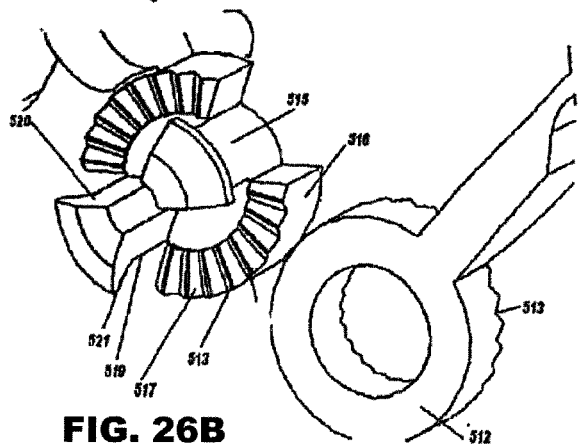

Referring to FIGS. 22 A, B and C there is shown a device (500) according to a tenth embodiment of the present invention for insertion within a nasal cavity. The device (500) is a unitary device which can be manufactured in a single step injection moulding process. The device includes a bridge (501) and two upstanding support members (502) extending substantially at right angles to the bridge and exhibiting symmetry about an axis defined by point A-A to form a rigid body structure. The upstanding support members (502) end in shoulders (503). The shoulders (503) generally exhibit an inverted U-shape structure extending from the body distal to the bridge, terminating in an enlarged end (504) which surface area rests flat against internal walls of a nasal cavity without causing discomforture of a user. The shoulders (503) include a first and second curved segment (505) and (506) respectively, separated by a living hinge (507) to enable the second segment (506) of the shoulder to pivot relative to the first segment (505).

The device (500) further includes a radial arm member (508) attached to and extending from the upstanding support members (502) at an acute angle by a living hinge. The arms (508) are able to move in a vertical plane in alignment with the upstanding support member(s), to describe an arcuate pathway. The arms (508) are biased laterally so that the arm, if moved away from the vertical plane defined by the upstanding support member, will be urged back towards its original position.

The arm member(s) (508) end in a circumferential ring (509) having oppositely facing surfaces (513 and 522) surrounding an opening (512). On one surface (513) of the ring (509) there is a series of teeth (510) being interlockable with corresponding mating teeth on a second arm member (511). The second arm member (511) extends from a surface adjacent the enlarged surface area (504) and is angled oppositely to the first arm member (508). The second arm member is joined at a surface near the enlarged surface area (504) by a living hinge which enables the second arm to pivot up and down in a substantially vertical plane. The second arm (511) ends in a protuberance (514) which includes an inner cylindrical core (515) with an outer core (516) encircling at least a part of the external wall of the inner core. The outer core has a first and second opposing face (517, 518) having teeth moulded onto the first face (517) for engagement with corresponding teeth (510) on the arm member (508).

The second arm (511) also includes a flange element (519) extending upwardly from the inner core (515). The flange (519) incorporates a neck (520) which passes through opening (512) in the circular protuberance (509) in an engaged condition, ending in a shoulder (521) that engages a surface (522) of the circumferential ring (509).

In an operating condition the device (500) requires arm member(s) (508) and (511) to be forced apart laterally against the natural bias so as to allow engagement of mating teeth on respective surfaces of circumferential ring (509) and protuberance (514). Prior to engagement of mating teeth the flange element (519) is passed through the opening (512) until the shoulder (521) of the flange rests against surface (522) of the circumferential ring. Once in an engaged condition the device (500) can be inserted within a users nasal cavity so that the bridge (501) spans the septum of a nose and the upstanding support members (502) bear against internal cavity walls. Once in an inserted condition a force can be applied against the engaged circumferential portions of the arms thereby to cause hinged movement of the arms relative to the support members. As the arms are displaced the interlocking teeth are urged over each other to allow corresponding outward displacement of the shoulder (506) about hinge (507). In this condition the enlarged area (504) of the arm exerts an opening pressure on the nasal wall to expand the nasal cavity.

In this embodiment the device can be retained in the nasal cavity in a suitably expanded state without inadvertent removal. The arms can be maintained in a relative position by the mating locking teeth. The shoulder portion (506) can be hingedly displaced outwardly by exerting a force against the interlocked ring (502) and protuberance (514) so as to enable the enlarged end to exert a desired pressure against the nasal wall. As a force is applied to the locked members the mating teeth disengage to enable hinged movement of the arms. When the nostril cavity is expanded sufficiently the teeth can be interlocked to retain the arms in the new/expanded condition. When the arms (508) and (511) are hingedly displaced in relation to the applied force, the shoulder portion (506) is correspondingly displaced outwardly about the living hinge (507) to enable the enlarged surface area (504) of the shoulder to exert a positive pressure against the internal walls of a nasal cavity.

In this embodiment the device can be adjusted manually insitu to open the nasal cavity. The upstanding support members of the device brace against one side of a nasal cavity while the shoulder portion (506) is pivotable about hinge (507) in concert with hinged movement of arm members (508) and (511) on application of an external force. The bridge (501) prevents the device from being inadvertently inhaled by a user and acts as a rigid support for bracing a surface of the nasal cavity wall. When the device adopts an expanded condition the enlarged end and the upright member(s) brace against the walls of the cavity and effectively prevent inadvertent removal of the device from the cavity.

Figure 27A:
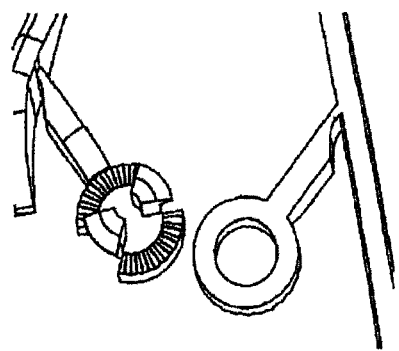
FIG. 27 A, B & C is a perspective view of a further embodiment in accordance with the present invention.
Figure 27B:
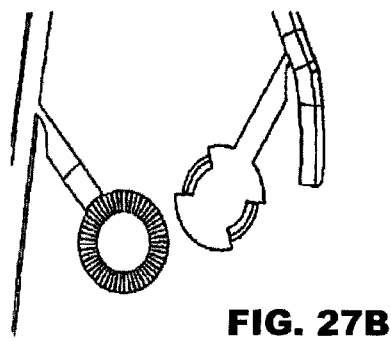
Figure 27C:
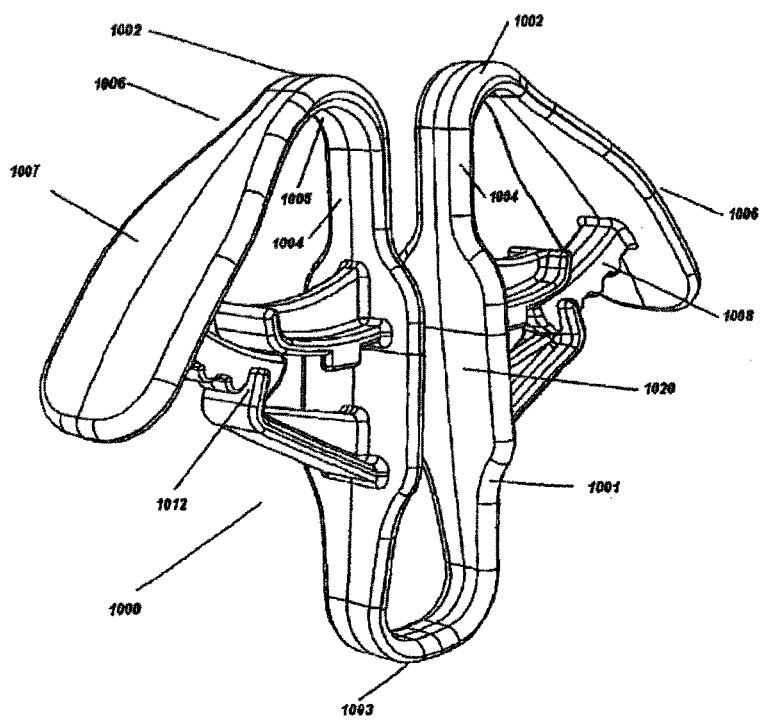
Figure 28A:
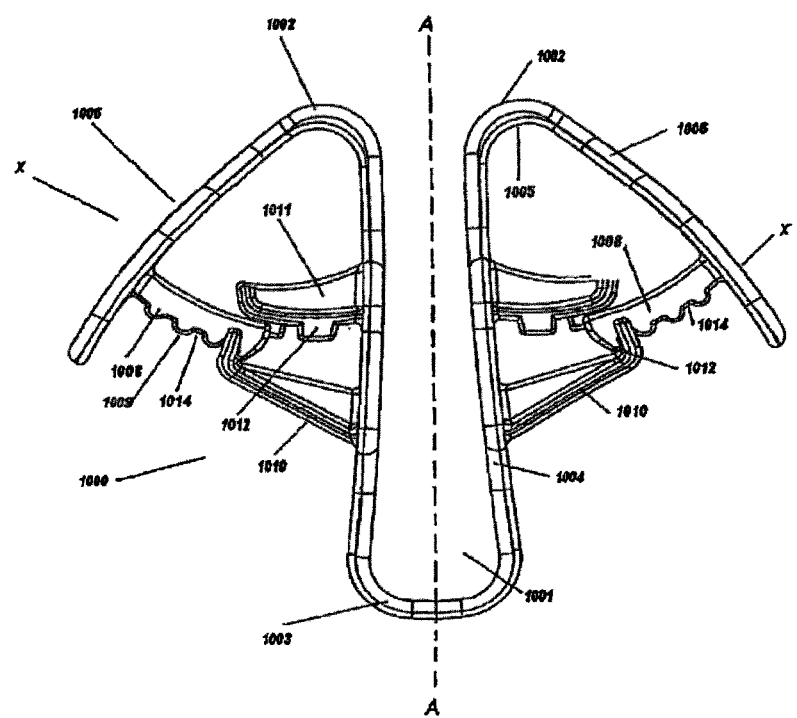
FIGS. 28 A, B & C represent the embodiment referred to in FIGS. 27 A, B & C in a front elevation, a plan view from beneath, and a plan view from above respectively.
Figure 28C:
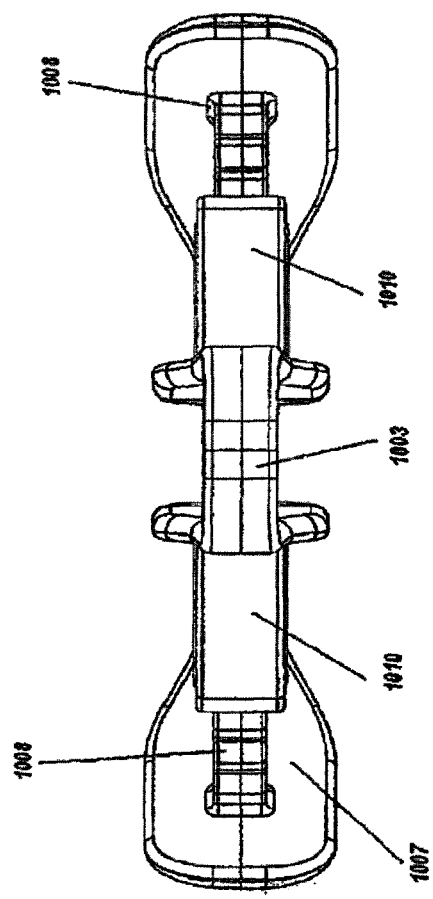

Referring to FIGS. 27 A, B & C there is shown a modification of the device illustrated in FIGS. 22 A, B and C. The modified nasal dilation device (1000) is preferably moulded in a single step process and includes a generally U-shaped body (1001) having an uppermost part (1002) and a lowermost part (1003) interconnected by a pair of spaced resilient upright members (1004). The modified device (1000) is symmetrical about axis A-A, best seen in FIG. 28A, hence for convenience an explanation is provided for one half of the device which will in turn apply for the equivalent opposite symmetrical feature.

The uppermost part of the U-shaped body extends outwardly at an angle to the upright member (1004) via a curved section (1005) to form a resilient rib or wing member (1006). The wing member (1006) includes a flattened section (1007) which in an operating condition rests against internal wall surfaces of a nasal cavity. The flattening and broadening of the wing section serves to increase the surface area in contact with internal cavity walls to spread the concentration of force exerted by the device over a wider surface as practicable.

The wing member (1006) includes an inwardly extending arm (1008) which has a series of resiliently spaced teeth (1009) separated by troughs (1014). The upright members (1004) of the body (1001) include two integrally formed and spaced apart arms (1010 and 1011) which extend outwardly towards the extending arm (1008) the spaced apart arms (1010 and 1011) being capable of engaging with the extending arm (1008) in an operating condition. Arm member (1011) includes a pair of downwardly extending flanges (1012) spaced apart to both receive and align arm member (1008) therebetween. Arm member (1010) includes a u-shaped recess (1013) adjacent its end for receiving troughs (1014). When troughs (1014) are engaged within the recess (1013), adjacent teeth (1009) rest on either side of the recess (1013) to maintain the wing member (1006) in a locked position at a constant angle to the body (1001).

Arm members (1010 and 1011) are resiliently formed relative to the upright members (1004) so that, when a force is applied to the wing members (1006) in the direction indicated by arrows (x), teeth members (1009) cause downward deflection of the arm (1010) as a tooth acts on a surface of the recess until an adjacent trough (1014) is engaged within the recess (1012). In this way adjustment of the angle between the wing member and the body can occur in a reversible manner. For example, referring to FIG. 28A, there is illustrated a modified device in a fully expanded condition. If it is desired to reduce the angle between the wing member and the body, a user/wearer is able to attend to adjustment by applying an external force against flattened sections (1007) of the wing member in the direction of (X).

In an insertion condition a trough closest to the wing member (1006) is engaged within the recess (1012) so that the angle between the wing and the body is reduced. Once inserted in a nasal cavity a user can apply an outwardly directed force on a lower inner surface of the wing member. Once the wing member is expanded sufficiently to promote increased airflow, the angle between the wing and the body is sustained by firm engagement of a trough between adjacent teeth within the recess.

In use the lowermost portion (1003) of the body is seated outside the nasal septum and upright members (1004) include a flat section (1020) which abuts internal wall structure of a nasal cavity. Generally at least the lower most portion of the body is transparent or flesh coloured so as to render the device inconspicuous from a casual observer.

Figure 30A:
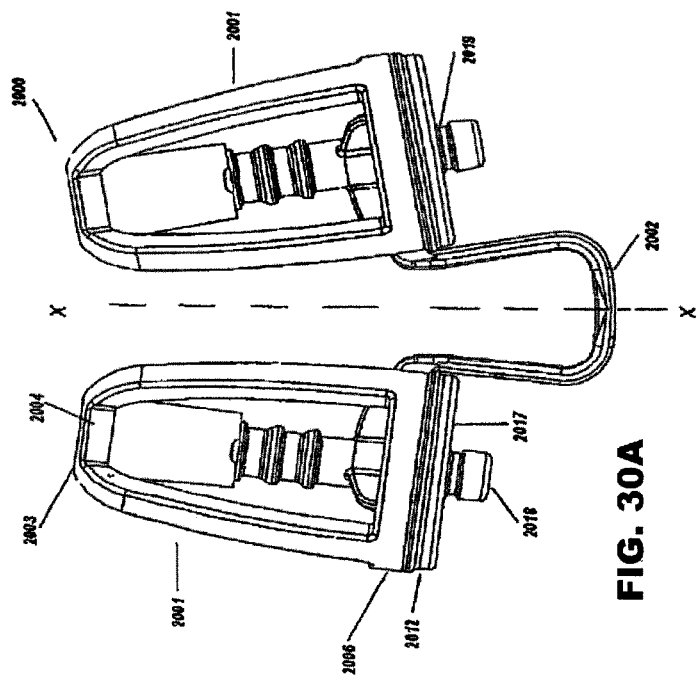
FIGS. 30 A, B & C represents the embodiment referred to in FIG. 29 by way of a front elevation, a plan view from above, and a plan view from beneath respectively.
Figure 30B:
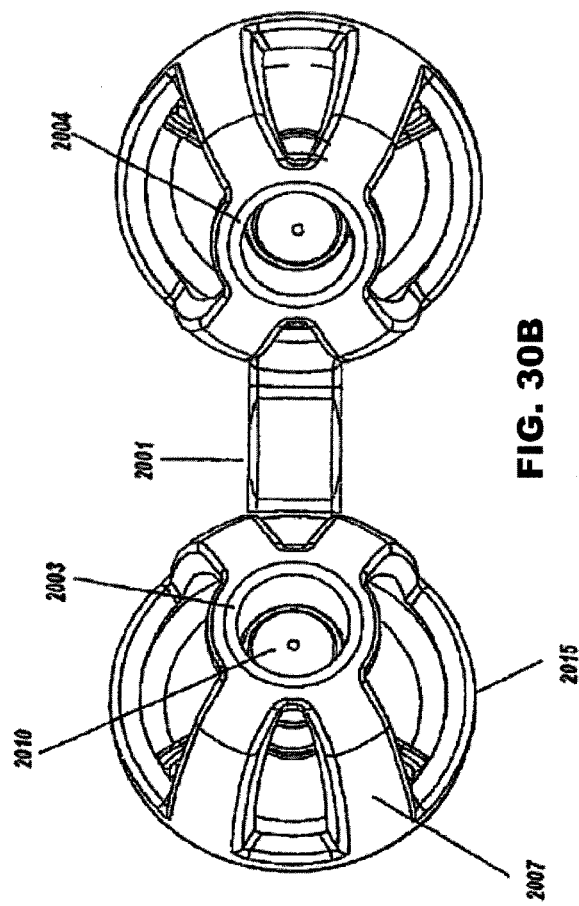
Figure 30C:
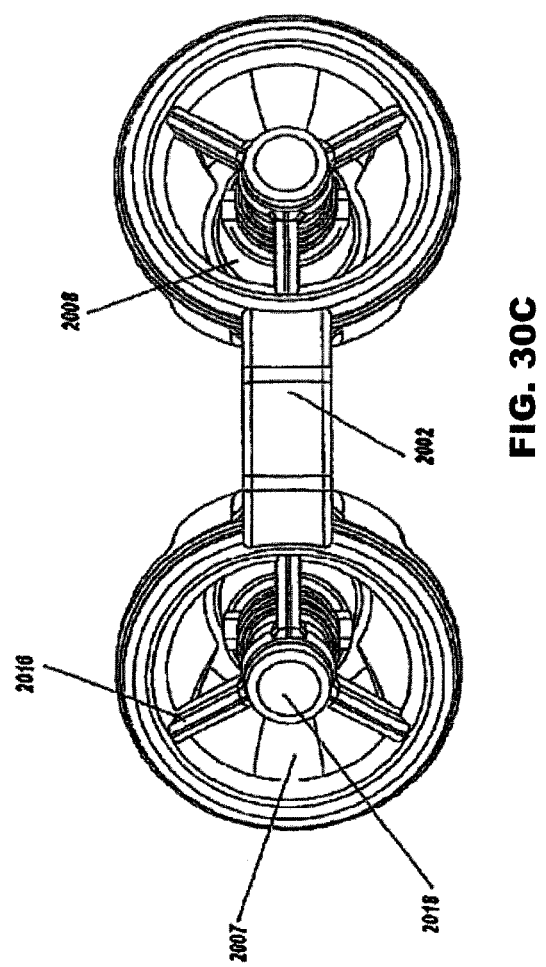

Referring to FIG. 29 and FIGS. 30 A, B and C there is shown a modification of the cage dilation system (2000) embodied in FIG. 20. The cage dilation system (2000) illustrated in FIG. 29 to FIGS. 30 A, B and C is divided into two body parts (2001) interconnected by a U-shaped bridge (2002). The two body parts exhibit symmetry about vertical axis XX', hence for convenience where reference is made to one body an identical component is present on the second body part. The body part (2001) includes an uppermost part (2003) forming a collar (2004) and a lowermost part (2005) forming a waistband (2006). The collar and waistband are integrally interconnected by a series of spaced flexible ribs (2007) which flex outwardly from the body describing an accurate pathway (not shown) when an external compressive force is applied against the uppermost and lower most ends.

The collar (2004) includes an integrally formed hollow cylindrical member (2008) located centrally and extending inwardly of the body.

The cage dilation system according to FIG. 29 and FIGS. 30 A, B and C further includes a holding means (2000) (best seen in FIG. 29). The holding means comprises:

a hollow cylindrical member (2008), formed integrally of the collar (2004), and located centrally and extending inwardly of the body; and a shaft (2010) extending upwardly and centrally from a holding base (2011).

The holding base includes a locking ring (2017) which has an annular shoulder (2012) that abuts the rim (2013) of the waistband when the shaft (2010) is engaged within the hollow cylinder (2008).

The holding base (2011) has a central platform (2015) from which the shaft (2010) extends upwardly to be received within the hollow cylinder (2008). The holding base also includes integral radial arm members (2016) interconnecting the central platform (2015) to the locking ring member (2017). The central platform (2015) includes a protrusion (2018) extending beneath the level of the locking ring. The protrusion (2018) has a recess (2019) (best seen in FIG. 30A) on which a vapour delivery system can be mounted (not shown).

The shaft (2010) has a series of spaced protrusions (2014) along its length which positively engage the internal surface of the hollow cylinder in an operating condition. It is generally understood that the internal diameter of the hollow cylinder is less than the external diameter of the protrusions so as to enable the protrusions to both deflect and positively engage the hollow cylinder as it moves through the cylinder.

In an operating condition (seen in FIG. 30A) the shaft (2010) is displaced through the opening of the hollow cylinder by applying an external force between the locking ring on the holding base and the collar (2004). Generally the cage system is fabricated from a resilient plastic material so that when the shaft enters the opening in the hollow cylinder the protrusions (2014) act against the internal surfaces of the hollow cylinder, thereby deflecting the internal surfaces to enable displacement and enabling positive engagement therewith. As the shaft is displaced along the hollow cylinder the flexible ribs (2007) extend outwardly to describe an accurate pathway. In use the ribs rest against internal wall surfaces of a user's nasal cavity. When the ribs are extended by applying a compressive force between the collar and the waistband, the walls of the nasal cavity against which the ribs are at rest, extend in response to the outward expansion of the ribs to promote flow of air through the cavity.

Figure 31C:
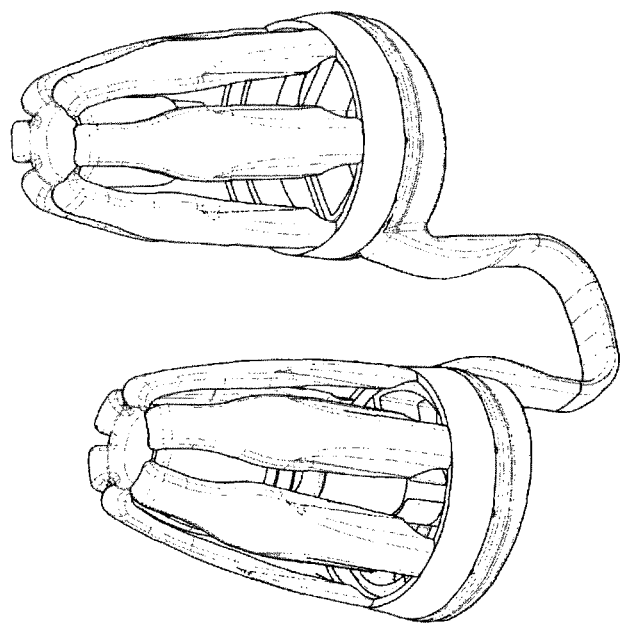

Referring to FIGS. 31 A, B & C there is shown a further embodiment of the device of the present invention. The device has a body (5008) with a flexible wall structure formed by a plurality of longitudinally extending elongated ribs (5032) extending between a top frame (5031) and a bottom frame (5033). From the top frame (5031) a longitudinal tubular sleeve member (5001) extends centrally of the body. The tubular sleeve member is formed by the each rib member folding inwardly of the body from the top frame end in an inverted U-shape cross-section, with webbing (5003) interspersed between each fold (5004). The bottom frame (5033) is a circular waistband which has a greater diameter than the top frame end so that the sizing of the device is such that it is insertable within the nasal cavity.

The cage dilation system (5000) illustrated in FIGS. 31 A, B and C is divided into two body parts interconnected by a U-shaped bridge (5005). The two body parts exhibit symmetry about vertical axis XX', hence for convenience where reference is made to one body an identical component is present on the second body part.

The device includes a holding base (5006) received within the waistband. The holding base includes a central platform connected thereto by radial components and a central member (5007) mounted on the platform extending upwardly therefrom and centrally of the body. The device also includes a holding means comprising oppositely disposed interlocking components. The interlocking components comprise the tubular sleeve member (5001) and opposing central member, wherein at least a part of the tubular sleeve and the central member include complementary mating means so that when a force is applied to one or both of the top or bottom frame ends the central member is received within the tubular sleeve and is held in a desired position. In this embodiment the tubular sleeve includes a series of teeth (5008) and the central member includes a series of mating teeth (5015) which interlock. In use when a force is applied to one or both of the top or bottom frame ends the rib members expand laterally. When a suitable size is obtained to sufficiently enlarge the nasal passage, the holding means maintain the size of the device until released. To aid comfort of a wearer, the rib members are shaped to include an enlarged mid-section thus optimizing the surface area of the ribs in contact with a surface of the nasal cavity wall.

In a further embodiment illustrated with reference to FIGS. 32 to 36, there is shown a nasal cavity device (6000) for combined flow of air through the nasal passage and a medicament or fragrance. The device includes a body (6001) shaped for insertion within a human nasal cavity. The body has a top frame end (6002) and a bottom frame end (6003) interconnected by a series of spaced apart ribs (6004). The body is made from a plastic material and the ribs structurally deform laterally (not shown) to exert a force on internal surfaces of a nasal cavity effective to improve airflow through the nasal passage of a wearer.

The device includes an expansion means (6005), which mounts the bottom frame end (6003) of the body. The expansion means comprises a base ring structure (6006) having an inner circumferential shoulder (6020) on which the bottom frame end is seated in an operating condition. The expansion means when mounted to the body defines a first airflow pathway within the device. The expansion means also includes a central housing structure (6021) comprising interrupted wall members such as a series of spaced apart legs (6009) interconnected to a centrally located platform (6022) wherein the legs extend substantially upwardly within the body from or adjacent to edge portions of the inner circumferential shoulder.

In this embodiment one end of the spaced legs end in shoulder portions (6023) which each connect directly to the central platform (6022). The other end of the spaced legs is mounted to the base ring structure by feet 6050. The feet include an opening (6060) to receive engaging portions (6051) of a bridge (6025).

As best seen in FIGS. 35 and 34, the device further includes a releasable locking system for releasably locking the expansion means and the body in operable engagement. The locking system consists of male and female interlocking components (6007) and (6008). Male component (6007) is mounted centrally of the expansion means by the interrupted wall members (6009). The female mating component (6008) extends centrally and inwardly of the body from the top frame end.

In an assembled condition (best seen in FIG. 32), the male and female interlockable components engage and thereby urge the expansion means against the bottom frame end. In a progressively engaged condition the top frame end and bottom frame end of the body are adjustably maintained at a desired distance effective for the flexible ribs to deform laterally to exert a desired dilating force on nasal for improving passage of air through the nasal cavity.

As can be seen the male component (6007) is elongate and includes a leading end (6010) and a threaded section (6011). The female component (6008) is located centrally of the body and is generally cylindrical and tapered between the top frame end and opening (6012). The leading end (6010) is generally larger than the opening (6012) and is adapted to be received within the opening of the female component and thereafter the threaded section frictionally engages inner sidewall portions of the female component. The threaded section allows both rotational and linear displacement of the male component within the female component.

In operation, as the male component is advanced by rotational or linear movement within the female component, a force is exerted against the bottom frame end by the expansion means causing rib members to deform laterally of the body.

As seen in FIGS. 35 and 39, the device further includes a demountable fragrance/medicament holder (6013) adapted to be mounted in the interrupted wall structure (6009) of the expansion means such that the fragrance holder and expansion means define a fragrance/medicament channel accessible to the first airflow pathway.

The fragrance holder includes a ring-like base structure being interconnected to a central holding structure (6015) having an interrupted well structure (6016) and an annular mounting structure (6014) with airflow cavities therebetween to allow mounting while allowing longitudinal ingress of airflow past the central holding means. In operation air flowing through the first airflow pathway passes into the fragrance channel for fragrance dispensing whereby fragrance merges with the first airflow pathways within the device.

In an assembled condition the central holding structure (6015) of the fragrance holder is received within the central housing structure (6021) of the expansion means, wherein the platform (6022) rests on the interrupted well structure (6016) thereby forming a roof for the central holding structure (6015). The fragrance holder includes a u-shaped recess (6026) within the ring-like base structure to accommodate an arm portion (6052) of the bridge member (6025).

In this embodiment of the invention the male component (6007) is mounted to the roof and extends into the body, and the female element (6008) is an oppositely disposed tubular sleeve structure extending within the body and wherein the male element is received in a releasable condition within the female element to substantially maintain the ribs in a desired deformed position to exert an effective force on internal surfaces of the nasal cavity walls.

The device as seen in FIG. 32 includes an outer sheath (6027) adapted to mount over the rib portion of the body. The sheath comprises a circumferential bottom frame end, which in use is supported on the outer circumferential platform of the expansion means, and spaced apart ribs extending upwardly from the circumferential bottom frame end ending in curved fingers (6028) for gripping attachment at the top frame end of the body.

As shown in FIGS. 32 and 36, the device can be joined to a second device by means of a bridge member (6025) whereby each device is adjusted independently or cojointly. The bridge member includes a generally symmetric u-shaped transparent structure (6029) ending in adjustable engaging portions (6051). The fragrance holder includes a recess (6026) in the base ring structure so that when the fragrance holder is mounted to the expansion means the recess accommodates a portion of the bridge member.

In a further preferred embodiment of the invention shown in FIG. 38, the device includes a demountable filter holder (6032) having an annular structure (6033) adapted to be mounted to a portion of the expansion means wherein the annular structure includes cavities to allow airflow. The mounting structure receives a filter member (6034) in a seated arrangement adjacent the nasal cavity opening. Air entering the first defined airflow pathway passes through the filter member and lateral deformation of the rib portion of the body is sufficient to exert an effective opening force on the nasal cavity walls to substantially minimize resistance to airflow by the filter member, The filter holder includes a circular base (6035) and annular mount portions (6033) adapted to engage receiving portions within the expansion means. The filter holder further includes radial arms (6036) and a semi-circular recess (6037) for receiving at least a portion of a bridging member. The filter member is a circular pad, the diameter of which is sized to abut wall surfaces of the nasal cavity.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A nasal dilation device comprising:
   a U-shaped body having a bridge portion and first and second upright members extending from the bridge portion; and
   first and second resilient wing members extending outwardly from and at an angle to the first and second upright members, respectively;
   the first and second wing members each comprising an inwardly extending arm;
   the first and second upright members each comprising an outwardly extending member;
   wherein the inwardly extending arms are arranged to engage with the respective outwardly extending members to provide an adjustment of the angle between the wing members and the first and second upright members, respectively;
   wherein the outwardly extending member comprises first and second outwardly extending arms spaced apart from each other.

2. The nasal dilator device of claim 1, wherein the outwardly extending member defines a recess arranged to receive the respective inwardly extending arm.

3. The nasal dilator device of claim 2, wherein the inwardly extending arm includes a series of teeth separated by troughs disposed thereon and wherein, when the inwardly extending arm is disposed within the recess, the troughs engage with the outwardly extending member to maintain the wing member in a fixed position at a constant angle to the body.

4. The nasal dilator device of claim 1, wherein the first outwardly extending arm includes a pair of flanges spaced apart to receive and align the inwardly extending arm therebetween.

5. The nasal dilator device of claim 4, wherein the second outwardly extending arm defines a U-shaped recess.

6. The nasal dilator device of claim 5, wherein the inwardly extending arm includes a series of teeth separated by troughs disposed thereon and wherein the U-shaped recess is arranged to receive and engage the troughs such that adjacent teeth rest on either side of the recess to maintain the wing member in a fixed position at an angle to the body.

7. The nasal dilation device of claim 1, wherein the first and second resilient wing members each comprise a curved section.

8. The nasal dilation device of claim 1, wherein the first and second resilient wing members each comprise a flattened section arranged, when in use, to rest against internal wall surfaces of a nasal cavity.

9. The nasal dilation device of claim 1, wherein the first and second upright members include a flat section arranged, when in use, to abut an internal wall structure of a nasal cavity.

10. The nasal dilation device of claim 1, wherein the outwardly extending members are integrally formed with the U-shaped body.

11. The nasal dilation device of claim 1, wherein the nasal dilation device is moulded in a single step process.

12. A nasal cavity dilation device including:
    an elongate U-shaped body; and
    a pair of symmetrical wing members having arcuate sections so that the pair of wings extend outwardly at an angle to the body;
    the body including a pair of outwardly extending members, each outwardly extending member extending towards a respective wing;
    each outwardly extending member comprising a first laterally extending arm and a second oppositely disposed laterally extending arm member, wherein the first arm member defines a recess;
    each wing member having a third arm member extending inwardly towards the first and second arm members so that the third arm member is receivable between the first and second arm members, the third arm member including a series of teeth separated by adjacent troughs which releasably engage with the first arm member; and
    wherein an angle of the wings relative to the body is controllable by adjusting the engagement between the adjacent troughs and recess.

13. The nasal cavity dilation device of claim 12, wherein the wing members include flattened sections arranged, in use, to rest against internal cavity walls.

14. The nasal cavity dilation device of claim 12, wherein the wing members are arranged to be expanded or contracted by urging the teeth against the recess until an adjacent trough engages the recess.

15. The nasal cavity dilation device of claim 12, wherein the arm including the recess is sufficiently resilient to enable teeth members to deflect the arm including the recess downwards as the teeth act against the recess.

* * * * *